(12) United States Patent
Nakamura et al.

(10) Patent No.: US 8,709,805 B2
(45) Date of Patent: Apr. 29, 2014

(54) CANINE IPS CELLS AND METHOD OF PRODUCING SAME

(75) Inventors: Tatsuo Nakamura, Kyoto (JP); Hidenori Shimada, Kyoto (JP)

(73) Assignee: Kyoto University, Kyoto (JP)

( * ) Notice: Subject to any disclaimer, the term of this patent is extended or adjusted under 35 U.S.C. 154(b) by 230 days.

(21) Appl. No.: 12/852,172

(22) Filed: Aug. 6, 2010

(65) Prior Publication Data

US 2011/0033936 A1    Feb. 10, 2011

(30) Foreign Application Priority Data

Aug. 7, 2009    (JP) ................................ 2009-185268

(51) Int. Cl.
| | |
|---|---|
| *C12N 5/00* | (2006.01) |
| *C12N 5/02* | (2006.01) |
| *C12N 15/00* | (2006.01) |
| *C12N 5/071* | (2010.01) |
| *C12N 5/10* | (2006.01) |

(52) U.S. Cl.
CPC ................ *C12N 5/0696* (2013.01); *C12N 5/10* (2013.01); *C12N 2501/115* (2013.01); *C12N 2501/602* (2013.01); *C12N 2501/603* (2013.01); *C12N 2501/604* (2013.01); *C12N 2501/606* (2013.01); *C12N 2501/998* (2013.01); *C12N 2501/999* (2013.01)
USPC ............................ 435/377; 435/350; 435/455

(58) Field of Classification Search
CPC .................................................... C12N 5/0696
USPC ....................................................... 435/377
See application file for complete search history.

(56) References Cited

U.S. PATENT DOCUMENTS

2009/0068742 A1    3/2009    Yamanaka

FOREIGN PATENT DOCUMENTS

| EP | 2 202 309 A1 | 6/2010 |
|---|---|---|
| WO | WO 2004/085631 A2 | 10/2004 |
| WO | WO 2007/069666 A1 | 6/2007 |
| WO | WO 2008/118820 A2 | 10/2008 |

OTHER PUBLICATIONS

Thomson et al. PNAS, 92:7844-7848 (Aug. 1995).*
NIH, Stem Cells: Scientific Progress and Future Research Directions, Department of Health and Human Services, Chapter 1, pp. 1-4, Jun. 2001).*
Djuric and Ellis, 2002, Stem Cell Research and Therapy, 2010,1:3.*
Lim et al. Proteomics, 2:1187-1203, 2002.*
James 2005, Development, 132:1273-1282.*
Silva, PLoS Biology, 2008, 6:2237-2247.*
Shi, 2008, Cell Stem Cell, 3:568-574.*
Huangfu, 2008, Nature Biotechnology, 26:795-797.*
Maherali, Cell Stem Cell, 2008:3:595.*
Daley, Cell Stem Cell, 2009:4:200-201.*
Ellis, Cell Stem Cell, 2009:4:198-199.*
Brons, Nature, 2007, 448:191-196.*
Esteban et al., *Cell Stem Cell*, 6: 71-79 (Jan. 8, 2010).
Ezashi et al., *PNAS*, 106(27): 10993-10998 (Jul. 7, 2009).
Feng et al., *Cell Stem Cell*, 4: 301-312 (Apr. 3, 2009).
Hatoya et al., *Mol. Reprod. Dev.*, 73: 298-305 (2006).
Hayes et al., *Stem Cells*, 26: 465-473 (2008).
Kim et al., *Cell Stem Cell*, 4(6): 472-476 (Jun. 5, 2009).
Lee et al., *Nature*, 436: 641 (Aug. 4, 2005).
Li et al., *Cell Stem Cell*, 4: 16-19 (Jan. 9, 2009).
Marson et al., *Cell Stem Cell*, 3: 132-135 (Aug. 7, 2008).
Mcmahon et al., *Cell*, 62: 1073-1085 (Sep. 21, 1990).
Nagaya, H., "Methods in Molecular Biology" (chapter 9) in *Reverse Chemical Genetics*, 577: 109-120 (Hisashi Koga (ed.), Humana Press, 2009).
Okita et al., *Nature*, 448: 313-317 (Jul. 19, 2007).
Okita et al., *Science*, 322: 949-953 (Nov. 7, 2008).
Schneider et al., *Human Molecular Genetics*, 17 (Review Issue 1): R42-R47 (2008).
Schneider et al., *Stem Cells*, 25: 1850-1851 (2007).
Shimada et al., *Mol. Reprod. Dev.*, 77(1): 2 (2010).
Takahashi et al., *Cell*, 126: 663-676 (Aug. 25, 2006).
Takahashi et al., *Cell*, 131: 861-872 (Nov. 30, 2007).
Vaags et al., *Stem Cells*, 27: 329-340 (2009).
Yamazoe et al., *Cell Transplantation*, 15: 135-145 (2006).
Yu et al., *Science*, 318: 1917-1920 (Dec. 21, 2007).
Zhao et al., *Cell Stem Cell*, 3: 475-479 (Nov. 6, 2008).
Zhou et al., *Cell Stem Cell*, 4: 381-384 (May 8, 2009).

* cited by examiner

*Primary Examiner* — Valarie Bertoglio
(74) *Attorney, Agent, or Firm* — Leydig, Voit & Mayer, Ltd.

(57) ABSTRACT

Provided are a method of producing canine iPS cells, comprising (a) the step of bringing into contact with each other a canine somatic cell and a nuclear reprogramming factor, and (b) the step of culturing the cell in a medium containing at least one substance selected from the group consisting of a mitogen-activated protein kinase kinase inhibitor, an activin receptor-like kinase inhibitor, a glycogen synthase kinase inhibitor, a L-type calcium channel agonist and a DNA methylation inhibitor, and a leukemia inhibitory factor, and canine iPS cells that can be obtained by the method.

7 Claims, 20 Drawing Sheets
(20 of 20 Drawing Sheet(s) Filed in Color)

FIG. 1-(a)
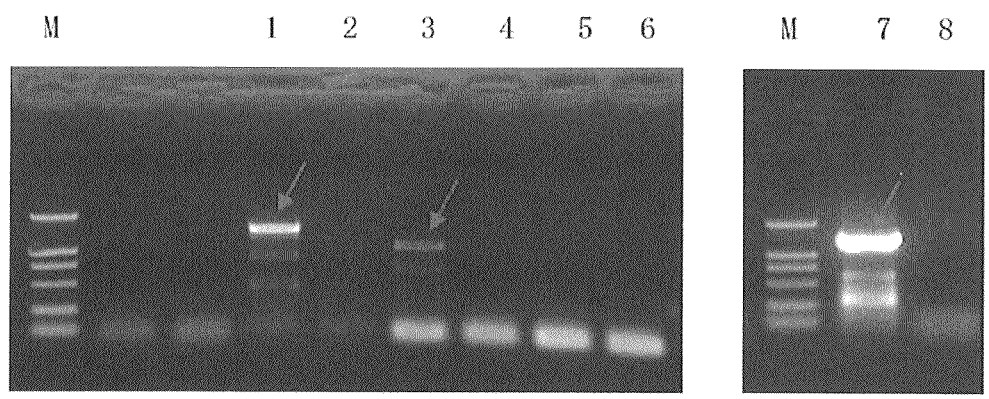
M SizeMarker
(2,000bp, 1,000bp, 750bp, 500bp, 250bp, 100bp from the top)
1% Agarose gel electrophoresis
1: Primer Set    C_KLF4      RT(+)
2: Primer Set    C_KLF4      RT(−)
3: Primer Set    C_OCT4      RT(+)
4: Primer Set    C_OCT4      RT(−)
5: Primer Set    C_SOX2      RT(+)
6: Primer Set    C_SOX2      RT(−)
7: Primer Set    C_C-Myc     RT(+) ※ 2nd PCR product
8: Primer Set    C_C-Myc     RT(−) ※ 2nd PCR product FIG. 1-(b)
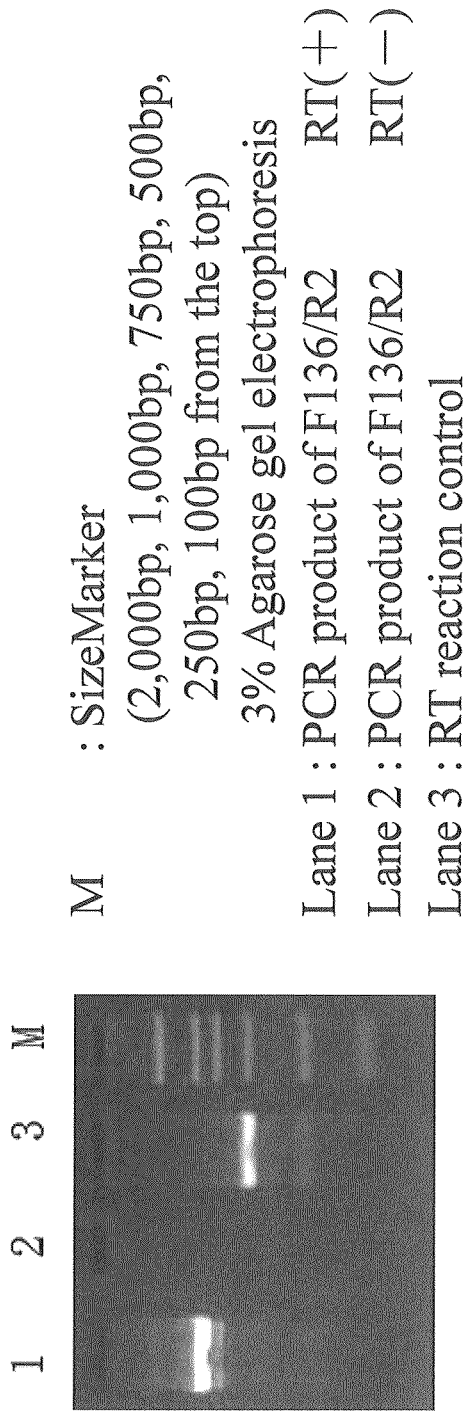
M : SizeMarker
(2,000bp, 1,000bp, 750bp, 500bp, 250bp, 100bp from the top)
3% Agarose gel electrophoresis
Lane 1 : PCR product of F136/R2  RT(+)
Lane 2 : PCR product of F136/R2  RT(−)
Lane 3 : RT reaction control FIG. 1-(C)
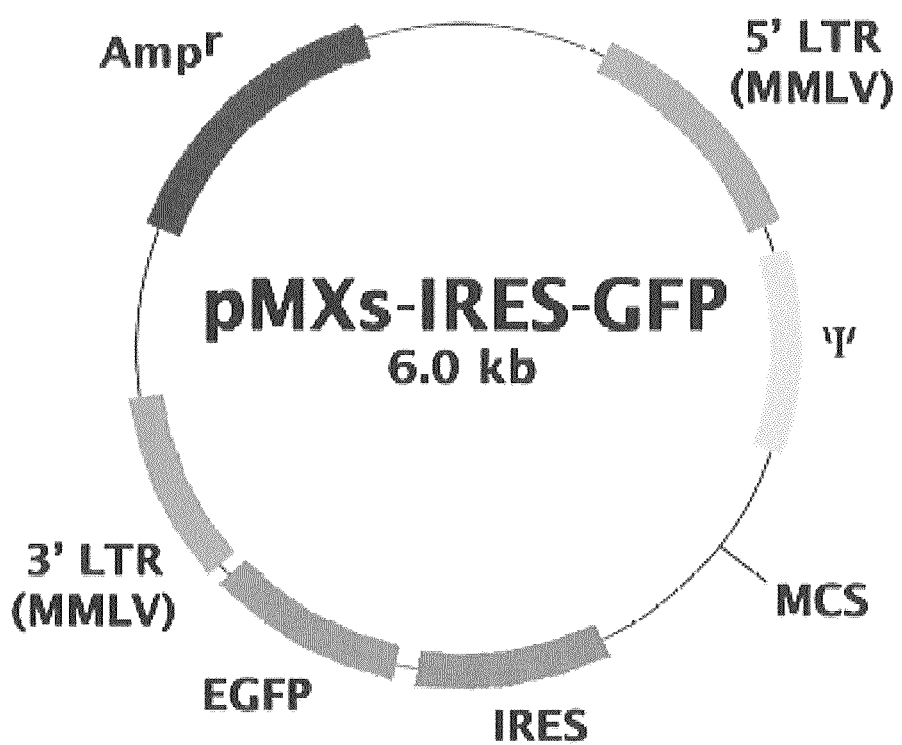

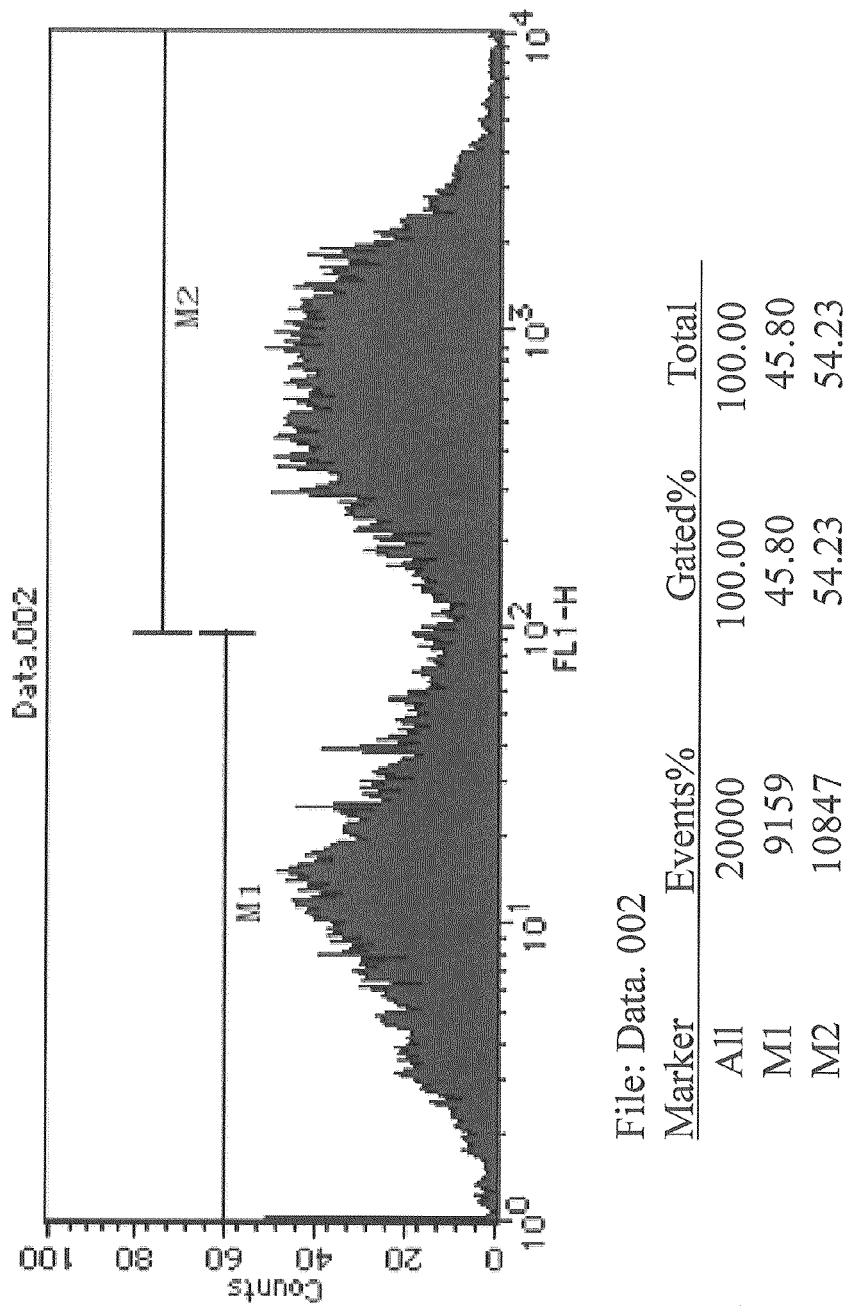
FIG. 3-(a)

FIG. 3-(b)
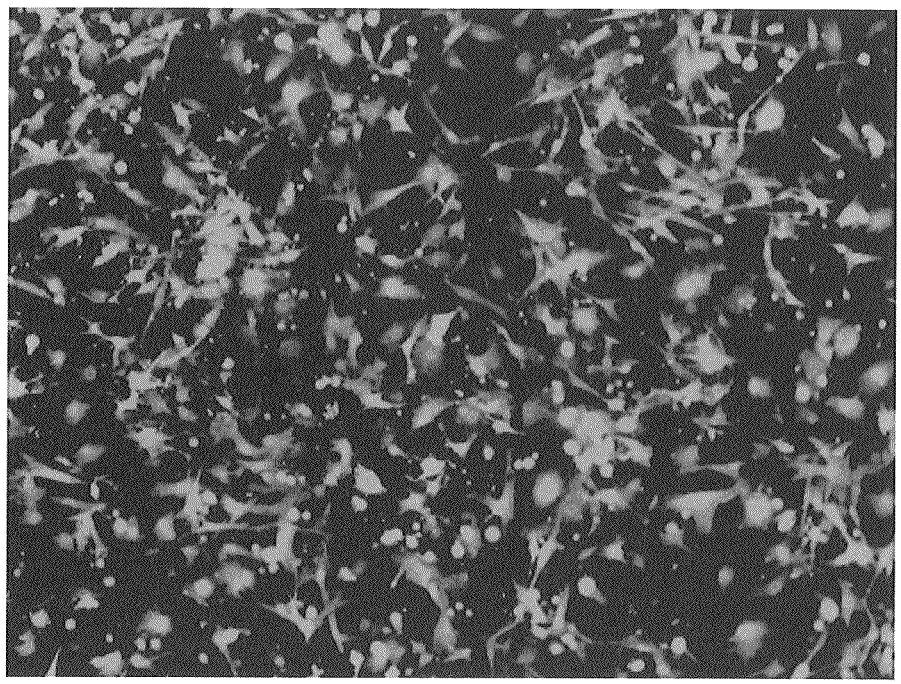

FIG. 4
(a)
(b)
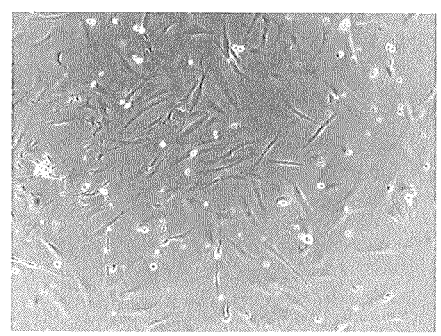
(c)
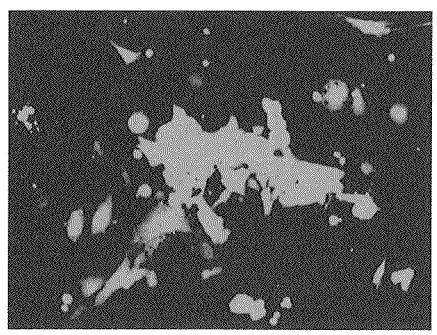
(d)
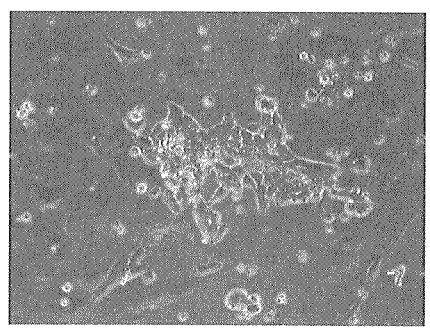

FIG. 5
(a)
(b)
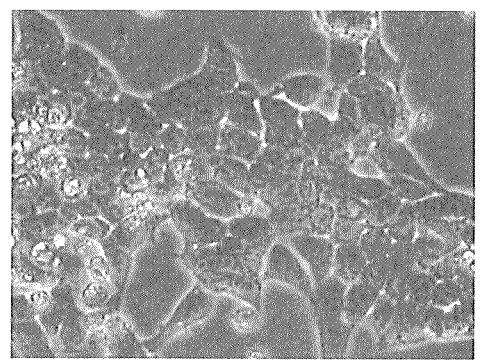
(c)
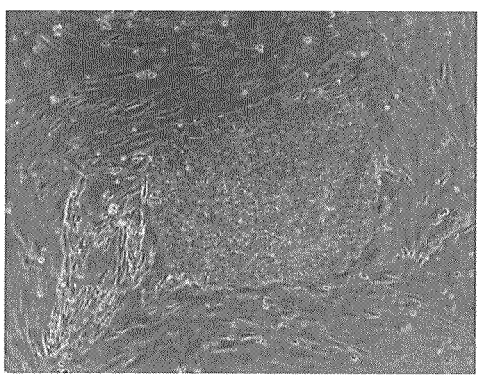
(d)
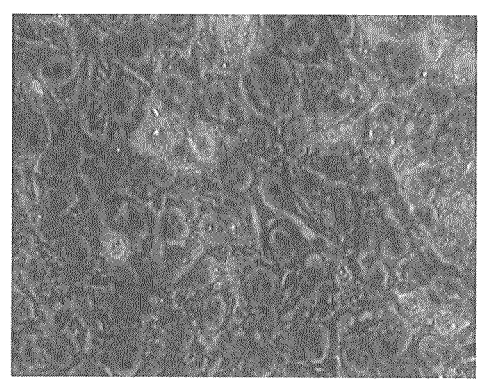

FIG.6-1
(a)
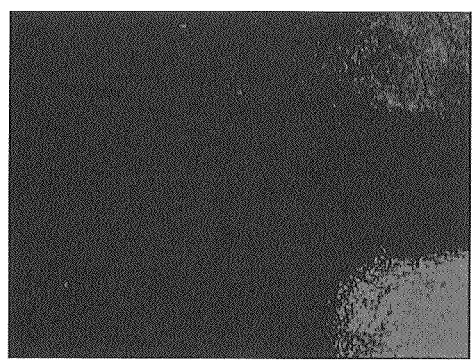
(b)
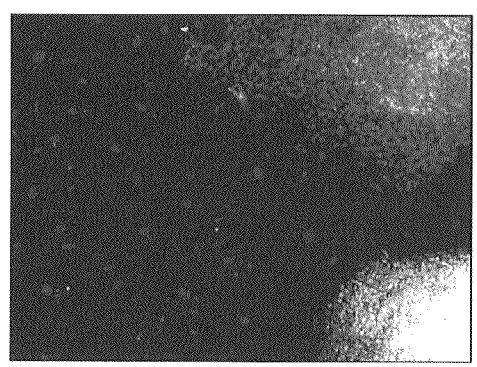
(c)
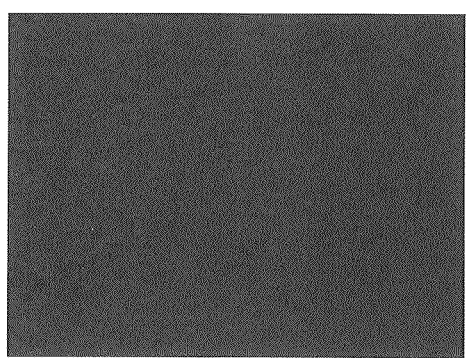
(d)
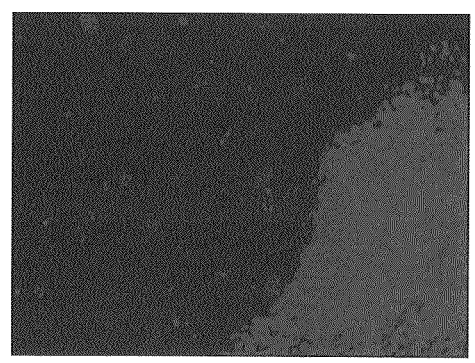

FIG. 6-2
(e)
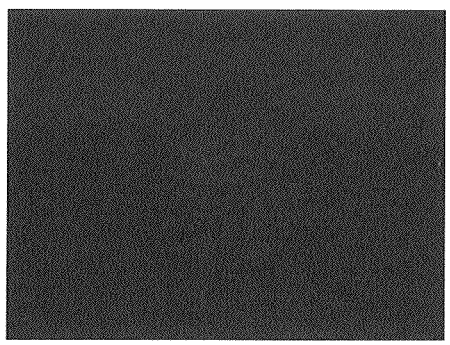
(f)
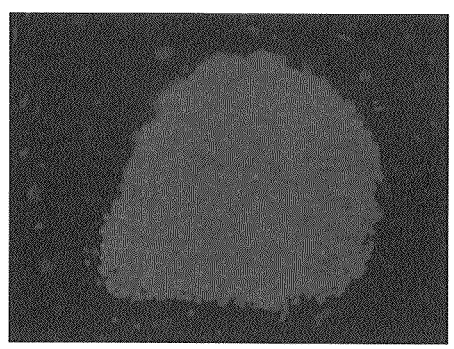
(g)
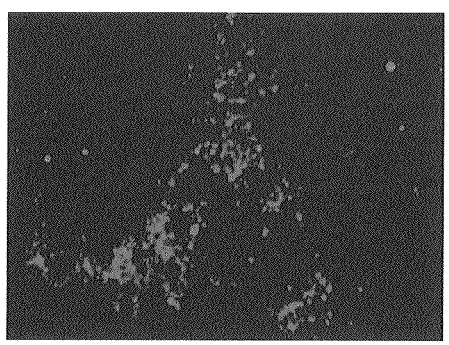
(h)
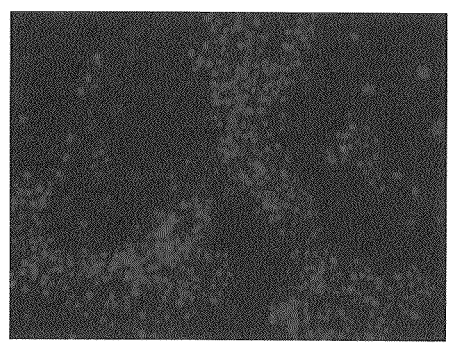
(i)
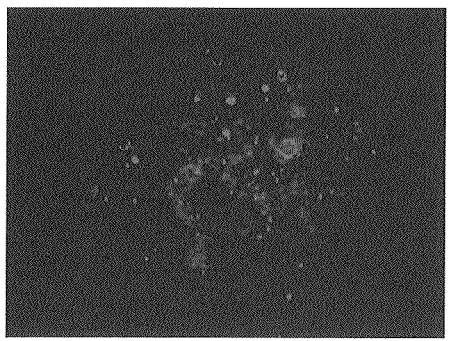
(j)
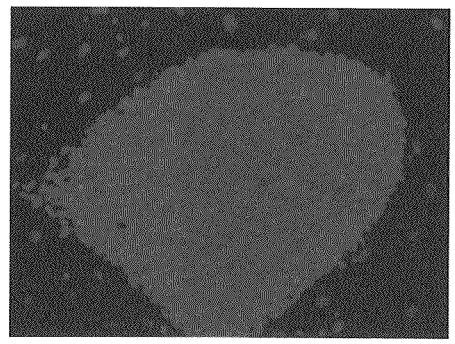

FIG. 7
(a) 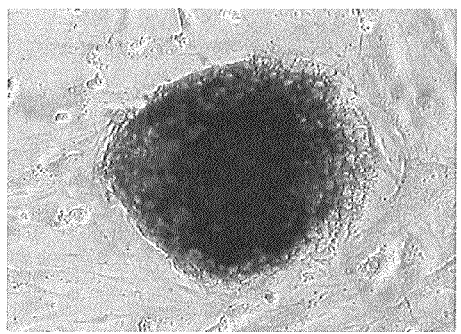
(b) 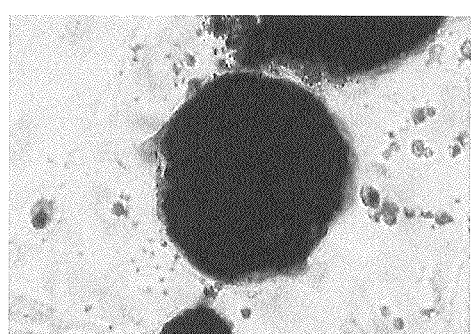

FIG. 8
(a)
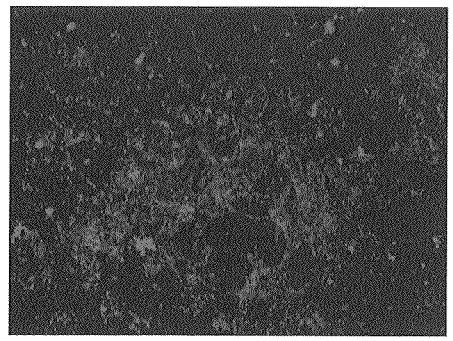
(b)
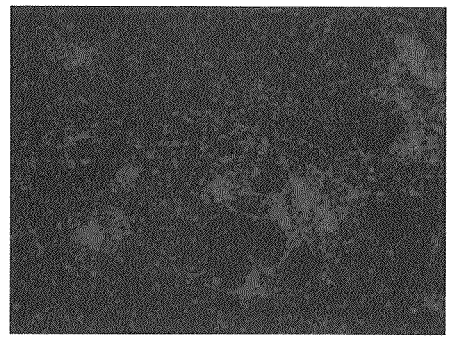
(c)
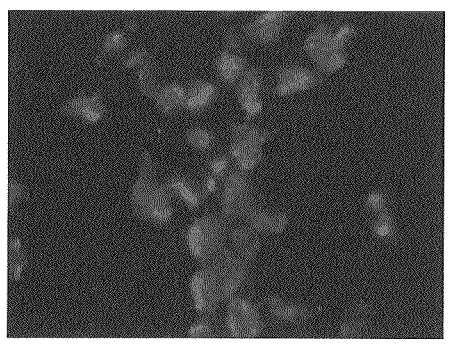
(d)
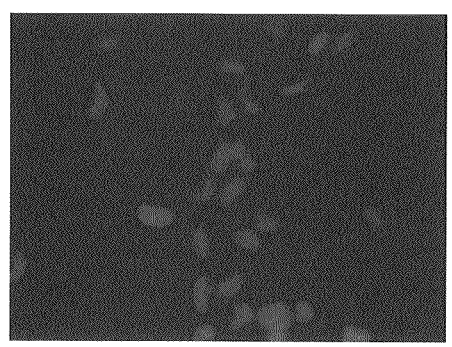
(e)
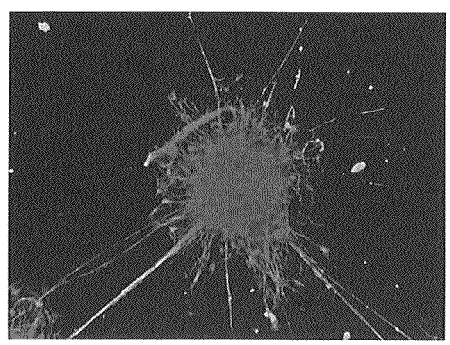
(f)
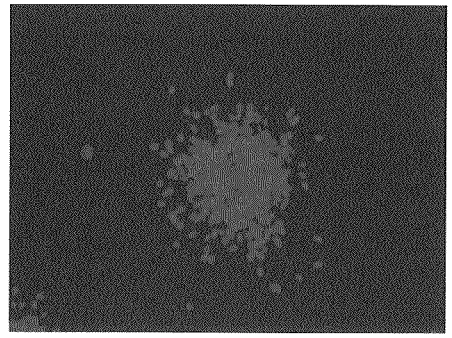

FIG. 13
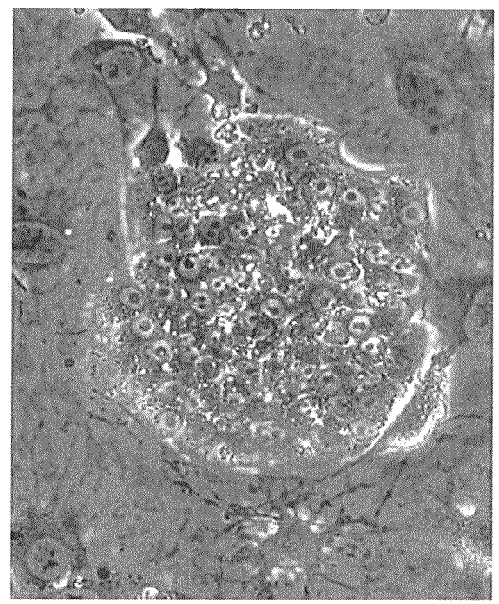
Canine iPS cells
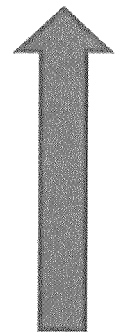
Canine adipose-derived cells

SEQUENCE LISTING

<160> NUMBER OF SEQ ID NOS: 23

<210> SEQ ID NO 1
<211> LENGTH: 1083
<212> TYPE: DNA
<213> ORGANISM: Canis lupus
<220> FEATURE:
<221> NAME/KEY: CDS
<222> LOCATION: (1)..(1083)
<223> OTHER INFORMATION: The 'Xaa' at location 82 stands for Met, or Leu.

<400> SEQUENCE: 1

```
atg gcg gga cac ctg gct tcc gac ttg gcc ttc tcg ccc ccg ccg ggc      48
Met Ala Gly His Leu Ala Ser Asp Leu Ala Phe Ser Pro Pro Pro Gly
1               5                   10                  15 ggt gga ggc gac ggg ccg gga ggg ccg gat ccc ggc tgg ggt gac ccc      96
Gly Gly Gly Asp Gly Pro Gly Gly Pro Asp Pro Gly Trp Gly Asp Pro
            20                  25                  30 cgg gcc tgg ctg agc ttc ccg ggg cct cca ggc ggg ccg gcc ctc ggg     144
Arg Ala Trp Leu Ser Phe Pro Gly Pro Pro Gly Gly Pro Ala Leu Gly
        35                  40                  45 ccc ggg gtc gga cct ggc gcc gag gtg tgg ggg ctc ccc ccg tgc ccc     192
Pro Gly Val Gly Pro Gly Ala Glu Val Trp Gly Leu Pro Pro Cys Pro
50                  55                  60 ccg ccc tat gag ttc tgc ggg ggg atg gcg tac tgt gga cct cag gtg     240
Pro Pro Tyr Glu Phe Cys Gly Gly Met Ala Tyr Cys Gly Pro Gln Val
65                  70                  75                  80 gga htg ggg ctg ctg ccc cga ggc ggc ccg gac acc tcc cag ccg gag     288
Gly Xaa Gly Leu Leu Pro Arg Gly Gly Pro Asp Thr Ser Gln Pro Glu
            85                  90                  95 ggc gag cgg gga gcc ggc ctg gag ggc agc tcc gag ggg gcc tcc ccc     336
Gly Glu Arg Gly Ala Gly Leu Glu Gly Ser Ser Glu Gly Ala Ser Pro
            100                 105                 110 gag ccc tgc gcc gcc ccg ccc ggg gtc gtg aag ccg gac aag gag aag     384
Glu Pro Cys Ala Ala Pro Pro Gly Val Val Lys Pro Asp Lys Glu Lys
        115                 120                 125 ctg gag caa aac ccc gag gag tcc caa gac atc aaa gcc ctg cag aaa     432
Leu Glu Gln Asn Pro Glu Glu Ser Gln Asp Ile Lys Ala Leu Gln Lys
130                 135                 140 gac ctg gag caa ttt gcc aag ctc ctg aag cag aag agg atc acc cta     480
Asp Leu Glu Gln Phe Ala Lys Leu Leu Lys Gln Lys Arg Ile Thr Leu
145                 150                 155                 160 gga tat act cag gcg gat gtg ggg ctc acc ctg ggg gtt ctc ttt ggg     528
Gly Tyr Thr Gln Ala Asp Val Gly Leu Thr Leu Gly Val Leu Phe Gly
                165                 170                 175 aag gtg ttc agc caa aca acc atc tgc cgt ttt gag gct ctg cag ctc     576
Lys Val Phe Ser Gln Thr Thr Ile Cys Arg Phe Glu Ala Leu Gln Leu
            180                 185                 190 agt ttc aag aat atg tgt aag ctg cgg ccc ctg ctg cag aag tgg gtg     624
Ser Phe Lys Asn Met Cys Lys Leu Arg Pro Leu Leu Gln Lys Trp Val
        195                 200                 205 gag gaa gct gac aac aat gaa aat cta cag gag ata tgc aaa gca gag     672
Glu Glu Ala Asp Asn Asn Glu Asn Leu Gln Glu Ile Cys Lys Ala Glu
210                 215                 220 acc ctc gtg cag gcc cga aag aga aag cga aca agc att gag aac cga     720
Thr Leu Val Gln Ala Arg Lys Arg Lys Arg Thr Ser Ile Glu Asn Arg
225                 230                 235                 240 gtg aga ggc aac ctg gag aac atg ttc ctg cag tgc ccg aag ccc acc     768
Val Arg Gly Asn Leu Glu Asn Met Phe Leu Gln Cys Pro Lys Pro Thr
                245                 250                 255 ctg cag cag atc agc cac att gcc cag cag ctc ggc ctt gag aag gat     816
Leu Gln Gln Ile Ser His Ile Ala Gln Gln Leu Gly Leu Glu Lys Asp
            260                 265                 270 gtg gtc cga gtg tgg ttc tgc aat cgt cgg cag aag ggc aaa cga tca     864
Val Val Arg Val Trp Phe Cys Asn Arg Arg Gln Lys Gly Lys Arg Ser
        275                 280                 285 agc agt gac tat tcg caa cga gag gat ttt gag gct gct ggg tcc cct     912
Ser Ser Asp Tyr Ser Gln Arg Glu Asp Phe Glu Ala Ala Gly Ser Pro
290                 295                 300
```

-continued

```
ttc tca ggg gca cca gta tcc ttt cct ctg gcg cca ggg ccc cat ttt    960
Phe Ser Gly Ala Pro Val Ser Phe Pro Leu Ala Pro Gly Pro His Phe
305                 310                 315                 320 ggt acc cca ggc tat ggg ggc cct cac ttc act acg ctc tac tcc tca   1008
Gly Thr Pro Gly Tyr Gly Gly Pro His Phe Thr Thr Leu Tyr Ser Ser
                325                 330                 335 gtc cct ctc cct gag ggt gaa ggc ttt ccc tct gtg tct gtc acc act   1056
Val Pro Leu Pro Glu Gly Glu Gly Phe Pro Ser Val Ser Val Thr Thr
                340                 345                 350 ctg ggc tct ccc atg cat tca aat tga                               1083
Leu Gly Ser Pro Met His Ser Asn
                355                 360

<210> SEQ ID NO 2
<211> LENGTH: 360
<212> TYPE: PRT
<213> ORGANISM: Canis lupus
<220> FEATURE:
<221> NAME/KEY: misc_feature
<222> LOCATION: (82)..(82)
<223> OTHER INFORMATION: The 'Xaa' at location 82 stands for Met, or
      Leu.

<400> SEQUENCE: 2

Met Ala Gly His Leu Ala Ser Asp Leu Ala Phe Ser Pro Pro Pro Gly
1               5                   10                  15

Gly Gly Gly Asp Gly Pro Gly Pro Asp Pro Gly Trp Gly Asp Pro
            20                  25                  30

Arg Ala Trp Leu Ser Phe Pro Gly Pro Pro Gly Gly Pro Ala Leu Gly
            35                  40                  45

Pro Gly Val Gly Pro Gly Ala Glu Val Trp Gly Leu Pro Pro Cys Pro
        50                  55                  60

Pro Pro Tyr Glu Phe Cys Gly Gly Met Ala Tyr Cys Gly Pro Gln Val
65                  70                  75                  80

Gly Xaa Gly Leu Leu Pro Arg Gly Gly Pro Asp Thr Ser Gln Pro Glu
                85                  90                  95

Gly Glu Arg Gly Ala Gly Leu Glu Gly Ser Ser Glu Gly Ala Ser Pro
            100                 105                 110

Glu Pro Cys Ala Ala Pro Pro Gly Val Val Lys Pro Asp Lys Glu Lys
        115                 120                 125

Leu Glu Gln Asn Pro Glu Glu Ser Gln Asp Ile Lys Ala Leu Gln Lys
    130                 135                 140

Asp Leu Glu Gln Phe Ala Lys Leu Leu Lys Gln Lys Arg Ile Thr Leu
145                 150                 155                 160

Gly Tyr Thr Gln Ala Asp Val Gly Leu Thr Leu Gly Val Leu Phe Gly
            165                 170                 175

Lys Val Phe Ser Gln Thr Thr Ile Cys Arg Phe Glu Ala Leu Gln Leu
        180                 185                 190

Ser Phe Lys Asn Met Cys Lys Leu Arg Pro Leu Leu Gln Lys Trp Val
    195                 200                 205

Glu Glu Ala Asp Asn Asn Glu Asn Leu Gln Glu Ile Cys Lys Ala Glu
    210                 215                 220

Thr Leu Val Gln Ala Arg Lys Arg Lys Arg Thr Ser Ile Glu Asn Arg
225                 230                 235                 240

Val Arg Gly Asn Leu Glu Asn Met Phe Leu Gln Cys Pro Lys Pro Thr
            245                 250                 255

Leu Gln Gln Ile Ser His Ile Ala Gln Gln Leu Gly Leu Glu Lys Asp
        260                 265                 270
```

```
Val Val Arg Val Trp Phe Cys Asn Arg Arg Gln Lys Gly Lys Arg Ser
        275                 280                 285
Ser Ser Asp Tyr Ser Gln Arg Glu Asp Phe Glu Ala Ala Gly Ser Pro
    290                 295                 300
Phe Ser Gly Ala Pro Val Ser Phe Pro Leu Ala Pro Gly Pro His Phe
305                 310                 315                 320
Gly Thr Pro Gly Tyr Gly Gly Pro His Phe Thr Thr Leu Tyr Ser Ser
                325                 330                 335
Val Pro Leu Pro Glu Gly Gly Phe Pro Ser Val Ser Val Thr Thr
                340                 345                 350
Leu Gly Ser Pro Met His Ser Asn
        355                 360

<210> SEQ ID NO 3
<211> LENGTH: 969
<212> TYPE: DNA
<213> ORGANISM: Canis lupus
<220> FEATURE:
<221> NAME/KEY: CDS
<222> LOCATION: (1)..(969)

<400> SEQUENCE: 3 atg tac aac atg atg gag acg gag ctg aag ccg ccg ggc ccg cag caa      48
Met Tyr Asn Met Met Glu Thr Glu Leu Lys Pro Pro Gly Pro Gln Gln
1               5                   10                  15 act tcg ggg ggc ggc ggc ggc ggc ggc ggc aac tcc acc gcg              96
Thr Ser Gly Gly Gly Gly Gly Gly Gly Gly Asn Ser Thr Ala
            20                  25                  30 gcg gcg gcg ggc ggc aac cag aag aac agc ccg gac cgc gtc aag cgg    144
Ala Ala Ala Gly Gly Asn Gln Lys Asn Ser Pro Asp Arg Val Lys Arg
        35                  40                  45 ccc atg aac gcc ttc atg gtg tgg tcc cgc ggg cag cgg cgc aag atg    192
Pro Met Asn Ala Phe Met Val Trp Ser Arg Gly Gln Arg Arg Lys Met
50                  55                  60 gcc cag gag aac ccc aag atg cac aac tcg gag atc agc aag cgc ctg    240
Ala Gln Glu Asn Pro Lys Met His Asn Ser Glu Ile Ser Lys Arg Leu
65                  70                  75                  80 ggc gcc gag tgg aaa ctt ttg tcg gag acg gag aag cgg ccg ttc atc    288
Gly Ala Glu Trp Lys Leu Leu Ser Glu Thr Glu Lys Arg Pro Phe Ile
                85                  90                  95 gac gag gcc aag cgg ctg cga gcg ctg cac atg aag gag cac ccg gat    336
Asp Glu Ala Lys Arg Leu Arg Ala Leu His Met Lys Glu His Pro Asp
            100                 105                 110 tat aaa tac cgg ccc cgg cgg aaa acc aag acg ctc atg aag aag gat    384
Tyr Lys Tyr Arg Pro Arg Arg Lys Thr Lys Thr Leu Met Lys Lys Asp
        115                 120                 125 aag tac acg ctg ccc ggc ggg ctg ctg gcc ccg ggc ggc aac agc atg    432
Lys Tyr Thr Leu Pro Gly Gly Leu Leu Ala Pro Gly Gly Asn Ser Met
    130                 135                 140 gcc agc ggg gtc ggg gtg ggc gcc ggc ctg ggc gcg ggc gtg aac cag    480
Ala Ser Gly Val Gly Val Gly Ala Gly Leu Gly Ala Gly Val Asn Gln
145                 150                 155                 160 cgc atg gac agc tac gcg cac atg aac ggc tgg agc aac ggc agc tac    528
Arg Met Asp Ser Tyr Ala His Met Asn Gly Trp Ser Asn Gly Ser Tyr
                165                 170                 175 agc atg atg cag gac cag ctg ggc tac ccg cag cac ccg ggc ctc aac    576
Ser Met Met Gln Asp Gln Leu Gly Tyr Pro Gln His Pro Gly Leu Asn
            180                 185                 190 gcg cac ggc gcc gcg cag atg cag ccc atg cac cgc tac gac gtg agc    624
Ala His Gly Ala Ala Gln Met Gln Pro Met His Arg Tyr Asp Val Ser
        195                 200                 205
```

```
gcc ctg cag tac aac tcc atg acc agc tcg cag acc tac atg aac ggc      672
Ala Leu Gln Tyr Asn Ser Met Thr Ser Ser Gln Thr Tyr Met Asn Gly
    210                 215                 220 tcg ccc acc tac agc atg tcc tac tcg cag cag ggc acc cct ggc atg      720
Ser Pro Thr Tyr Ser Met Ser Tyr Ser Gln Gln Gly Thr Pro Gly Met
225                 230                 235                 240 gcg ctg ggc tcc atg ggc tcg gtg gtc aag tcc gag gcc agc tcc agc      768
Ala Leu Gly Ser Met Gly Ser Val Val Lys Ser Glu Ala Ser Ser Ser
                245                 250                 255 ccc ccc gtg gtt acc tcc tcc tcc cac tcc agg gcg ccc tgc cag gcc      816
Pro Pro Val Val Thr Ser Ser Ser His Ser Arg Ala Pro Cys Gln Ala
            260                 265                 270 ggg gac ctc cgg gac atg atc agc atg tac ctc ccc ggc gcc gag gtg      864
Gly Asp Leu Arg Asp Met Ile Ser Met Tyr Leu Pro Gly Ala Glu Val
        275                 280                 285 ccg gag ccc gcc gcc ccc agc aga ctg cac atg tcc cag cac tac cag      912
Pro Glu Pro Ala Ala Pro Ser Arg Leu His Met Ser Gln His Tyr Gln
    290                 295                 300 agc ggc ccg gtg ccc ggc acg gcc att aac ggc aca ctg ccc ctc tcg      960
Ser Gly Pro Val Pro Gly Thr Ala Ile Asn Gly Thr Leu Pro Leu Ser
305                 310                 315                 320 cac atg tga                                                          969
His Met <210> SEQ ID NO 4
<211> LENGTH: 322
<212> TYPE: PRT
<213> ORGANISM: Canis lupus

<400> SEQUENCE: 4

Met Tyr Asn Met Met Glu Thr Glu Leu Lys Pro Pro Gly Pro Gln Gln
1               5                   10                  15

Thr Ser Gly Gly Gly Gly Gly Gly Gly Gly Asn Ser Thr Ala
            20                  25                  30

Ala Ala Ala Gly Gly Asn Gln Lys Asn Ser Pro Asp Arg Val Lys Arg
        35                  40                  45

Pro Met Asn Ala Phe Met Val Trp Ser Arg Gly Gln Arg Arg Lys Met
    50                  55                  60

Ala Gln Glu Asn Pro Lys Met His Asn Ser Glu Ile Ser Lys Arg Leu
65                  70                  75                  80

Gly Ala Glu Trp Lys Leu Leu Ser Glu Thr Glu Lys Arg Pro Phe Ile
                85                  90                  95

Asp Glu Ala Lys Arg Leu Arg Ala Leu His Met Lys Glu His Pro Asp
            100                 105                 110

Tyr Lys Tyr Arg Pro Arg Arg Lys Thr Lys Thr Leu Met Lys Lys Asp
        115                 120                 125

Lys Tyr Thr Leu Pro Gly Gly Leu Leu Ala Pro Gly Gly Asn Ser Met
    130                 135                 140

Ala Ser Gly Val Gly Val Gly Ala Gly Leu Gly Ala Gly Val Asn Gln
145                 150                 155                 160

Arg Met Asp Ser Tyr Ala His Met Asn Gly Trp Ser Asn Gly Ser Tyr
                165                 170                 175

Ser Met Met Gln Asp Gln Leu Gly Tyr Pro Gln His Pro Gly Leu Asn
            180                 185                 190

Ala His Gly Ala Ala Gln Met Gln Pro Met His Arg Tyr Asp Val Ser
        195                 200                 205

Ala Leu Gln Tyr Asn Ser Met Thr Ser Ser Gln Thr Tyr Met Asn Gly
```

```
                 210                 215                 220
Ser Pro Thr Tyr Ser Met Ser Tyr Ser Gln Gln Gly Thr Pro Gly Met
225                 230                 235                 240

Ala Leu Gly Ser Met Gly Ser Val Val Lys Ser Glu Ala Ser Ser Ser
                245                 250                 255

Pro Pro Val Val Thr Ser Ser His Ser Arg Ala Pro Cys Gln Ala
            260                 265                 270

Gly Asp Leu Arg Asp Met Ile Ser Met Tyr Leu Pro Gly Ala Glu Val
            275                 280                 285

Pro Glu Pro Ala Ala Pro Ser Arg Leu His Met Ser Gln His Tyr Gln
        290                 295                 300

Ser Gly Pro Val Pro Gly Thr Ala Ile Asn Gly Thr Leu Pro Leu Ser
305                 310                 315                 320

His Met

<210> SEQ ID NO 5
<211> LENGTH: 1446
<212> TYPE: DNA
<213> ORGANISM: Canis lupus
<220> FEATURE:
<221> NAME/KEY: CDS
<222> LOCATION: (1)..(1446)

<400> SEQUENCE: 5 atg gct gtc agc gac gct ctg ctc ccg tcc ttc tcc acg ttc gcg tcc      48
Met Ala Val Ser Asp Ala Leu Leu Pro Ser Phe Ser Thr Phe Ala Ser
1               5                   10                  15 ggc ccg gcg gga agg gag aag acc ctg cgt cca gca ggt gcc ccg aat      96
Gly Pro Ala Gly Arg Glu Lys Thr Leu Arg Pro Ala Gly Ala Pro Asn
            20                  25                  30 aac cgc tgg cgg gag gag ctc tcg cac atg aag cga ctt ccc ccg gtg     144
Asn Arg Trp Arg Glu Glu Leu Ser His Met Lys Arg Leu Pro Pro Val
        35                  40                  45 ctc ccc ggc cgc ccc tac gac ctg gcg gcg gcg acc gtg gcc ccc gac     192
Leu Pro Gly Arg Pro Tyr Asp Leu Ala Ala Ala Thr Val Ala Pro Asp
    50                  55                  60 ctg gaa ggt ggc gga gtc ggc gcg gcc tgt ggc ggc agc aac ccc gct     240
Leu Glu Gly Gly Gly Val Gly Ala Ala Cys Gly Gly Ser Asn Pro Ala
65                  70                  75                  80 ctg cta ccc cgg agg gag acg gag gag ttc aac gac ctc ctg gac ctg     288
Leu Leu Pro Arg Arg Glu Thr Glu Glu Phe Asn Asp Leu Leu Asp Leu
                85                  90                  95 gac ttc atc ctc tcc aac tcg ctg tcc cac ccg gag tcc gtg gcc gcc     336
Asp Phe Ile Leu Ser Asn Ser Leu Ser His Pro Glu Ser Val Ala Ala
            100                 105                 110 acc gtg tcc tcg tcg gcg tcg gcc tcg tcg tcc tcg ccg tcg agc         384
Thr Val Ser Ser Ser Ala Ser Ala Ser Ser Ser Ser Ser Pro Ser Ser
        115                 120                 125 agc ggt gcg gcc agt gca ccc tcc acc tgc agc ttc agc tac ccg atc     432
Ser Gly Ala Ala Ser Ala Pro Ser Thr Cys Ser Phe Ser Tyr Pro Ile
    130                 135                 140 cgg gcc ggg ggg gac ccg ggc gtg gcg ccg ggc ggc ggt ggc ggc         480
Arg Ala Gly Gly Asp Pro Gly Val Ala Pro Gly Gly Gly Gly Gly Gly
145                 150                 155                 160 ggc ggc ggc ggc ctc ctc tac agc cgg gag ccc gtg ccc cct ccc         528
Gly Gly Gly Gly Gly Leu Leu Tyr Ser Arg Glu Pro Val Pro Pro Pro
                165                 170                 175 acg gcc ccc ttc aat ctg gcg gac atc aac gac gtg agc ccc tcg ggc     576
Thr Ala Pro Phe Asn Leu Ala Asp Ile Asn Asp Val Ser Pro Ser Gly
            180                 185                 190
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ggc | ttc | gtg | gct | gag | ctc | ctt | cgg | ccc | gag | ttg | gac | cca | gtg | tac | att | 624  |
| Gly | Phe | Val | Ala | Glu | Leu | Leu | Arg | Pro | Glu | Leu | Asp | Pro | Val | Tyr | Ile |      |
|     |     | 195 |     |     |     | 200 |     |     |     |     | 205 |     |     |     |     |      |

```
ccg ccg cag cag ccg cag ccg cca ggt ggc ggg ctg atg ggc aag ttc     672
Pro Pro Gln Gln Pro Gln Pro Pro Gly Gly Gly Leu Met Gly Lys Phe
        210                 215                 220 gtg ctg aag gcg tcg ctg agc gcc ccc ggc agc gag tac ggc agc ccg     720
Val Leu Lys Ala Ser Leu Ser Ala Pro Gly Ser Glu Tyr Gly Ser Pro
225                 230                 235                 240 tcg gtc atc agt gtt agc aag ggc agc ccg gat ggc agc cac ccg gtg     768
Ser Val Ile Ser Val Ser Lys Gly Ser Pro Asp Gly Ser His Pro Val
                    245                 250                 255 gtc gtg gcg ccc tac agc ggc ggc ccg ccg cgc atg tgc ccc aag atc     816
Val Val Ala Pro Tyr Ser Gly Gly Pro Pro Arg Met Cys Pro Lys Ile
                260                 265                 270 aag cag gag gcg gtc tcg tcg tgc acg gtc ggc cgg ccc ctg gag gcc     864
Lys Gln Glu Ala Val Ser Ser Cys Thr Val Gly Arg Pro Leu Glu Ala
            275                 280                 285 cac ttg ggc acc gga ccc cct ctc agc aac ggc cac cgg ccg cca gcg     912
His Leu Gly Thr Gly Pro Pro Leu Ser Asn Gly His Arg Pro Pro Ala
        290                 295                 300 cac gac ttc ccc ctg ggg cgg cag ctc ccc agc agg act acc ccg acc     960
His Asp Phe Pro Leu Gly Arg Gln Leu Pro Ser Arg Thr Thr Pro Thr
305                 310                 315                 320 ctg ggt gcc gag gaa ctg ctg agc agc agg gac tgt cac ccc gcc cta    1008
Leu Gly Ala Glu Glu Leu Leu Ser Ser Arg Asp Cys His Pro Ala Leu
                    325                 330                 335 cca ctc ccc ccg ggc ttt cac ccc cac ccc ggg ccc aac tac ccg ccc    1056
Pro Leu Pro Pro Gly Phe His Pro His Pro Gly Pro Asn Tyr Pro Pro
                340                 345                 350 ttt ttg cca gac cag atg cag cca cag gtc cca ccg ctc cat tac caa    1104
Phe Leu Pro Asp Gln Met Gln Pro Gln Val Pro Pro Leu His Tyr Gln
            355                 360                 365 gag ctc atg cct cct ggt tcc tgc atg ccg gag gag ccg aaa cca aag    1152
Glu Leu Met Pro Pro Gly Ser Cys Met Pro Glu Glu Pro Lys Pro Lys
        370                 375                 380 agg ggg aga agg tca tgg ccc cgg aaa agg aca gcc act cac act tgt    1200
Arg Gly Arg Arg Ser Trp Pro Arg Lys Arg Thr Ala Thr His Thr Cys
385                 390                 395                 400 gat tat gcg ggc tgc ggc aaa acc tac acg aag agt tct cat ctc aag    1248
Asp Tyr Ala Gly Cys Gly Lys Thr Tyr Thr Lys Ser Ser His Leu Lys
                    405                 410                 415 gca cac ctg cga acc cac aca ggt gag aaa ccc tac cac tgt gat tgg    1296
Ala His Leu Arg Thr His Thr Gly Glu Lys Pro Tyr His Cys Asp Trp
                420                 425                 430 gac ggc tgt ggg tgg aaa ttc gcc cgc tcg gac gaa ctg acg agg cac    1344
Asp Gly Cys Gly Trp Lys Phe Ala Arg Ser Asp Glu Leu Thr Arg His
            435                 440                 445 tac cgc aaa cac acc ggg cac cgc ccc ttc cag tgc cag aag tgc gac    1392
Tyr Arg Lys His Thr Gly His Arg Pro Phe Gln Cys Gln Lys Cys Asp
        450                 455                 460 agg gcc ttc tcc agg tcg gac cac ctc gcc tta cac atg aag agg cac    1440
Arg Ala Phe Ser Arg Ser Asp His Leu Ala Leu His Met Lys Arg His
465                 470                 475                 480 ttt taa                                                            1446
Phe

<210> SEQ ID NO 6
<211> LENGTH: 481
<212> TYPE: PRT
```

-continued

<213> ORGANISM: Canis lupus

<400> SEQUENCE: 6

```
Met Ala Val Ser Asp Ala Leu Leu Pro Ser Phe Ser Thr Phe Ala Ser
1               5                   10                  15

Gly Pro Ala Gly Arg Glu Lys Thr Leu Arg Pro Ala Gly Ala Pro Asn
            20                  25                  30

Asn Arg Trp Arg Glu Glu Leu Ser His Met Lys Arg Leu Pro Pro Val
        35                  40                  45

Leu Pro Gly Arg Pro Tyr Asp Leu Ala Ala Thr Val Ala Pro Asp
    50                  55                  60

Leu Glu Gly Gly Gly Val Gly Ala Ala Cys Gly Gly Ser Asn Pro Ala
65                  70                  75                  80

Leu Leu Pro Arg Arg Glu Thr Glu Glu Phe Asn Asp Leu Leu Asp Leu
                85                  90                  95

Asp Phe Ile Leu Ser Asn Ser Leu Ser His Pro Glu Ser Val Ala Ala
            100                 105                 110

Thr Val Ser Ser Ser Ala Ser Ser Ser Ser Ser Pro Ser Ser
        115                 120                 125

Ser Gly Ala Ala Ser Ala Pro Ser Thr Cys Ser Phe Ser Tyr Pro Ile
130                 135                 140

Arg Ala Gly Gly Asp Pro Gly Val Ala Pro Gly Gly Gly Gly Gly
145                 150                 155                 160

Gly Gly Gly Gly Leu Leu Tyr Ser Arg Glu Pro Val Pro Pro
            165                 170                 175

Thr Ala Pro Phe Asn Leu Ala Asp Ile Asn Asp Val Ser Pro Ser Gly
            180                 185                 190

Gly Phe Val Ala Glu Leu Leu Arg Pro Glu Leu Asp Pro Val Tyr Ile
            195                 200                 205

Pro Pro Gln Gln Pro Gln Pro Pro Gly Gly Gly Leu Met Gly Lys Phe
        210                 215                 220

Val Leu Lys Ala Ser Leu Ser Ala Pro Gly Ser Glu Tyr Gly Ser Pro
225                 230                 235                 240

Ser Val Ile Ser Val Ser Lys Gly Ser Pro Asp Gly Ser His Pro Val
            245                 250                 255

Val Val Ala Pro Tyr Ser Gly Gly Pro Pro Arg Met Cys Pro Lys Ile
            260                 265                 270

Lys Gln Glu Ala Val Ser Ser Cys Thr Val Gly Arg Pro Leu Glu Ala
        275                 280                 285

His Leu Gly Thr Gly Pro Pro Leu Ser Asn Gly His Arg Pro Pro Ala
    290                 295                 300

His Asp Phe Pro Leu Gly Arg Gln Leu Pro Ser Arg Thr Thr Pro Thr
305                 310                 315                 320

Leu Gly Ala Glu Glu Leu Leu Ser Ser Arg Asp Cys His Pro Ala Leu
                325                 330                 335

Pro Leu Pro Pro Gly Phe His Pro His Pro Gly Pro Asn Tyr Pro Pro
            340                 345                 350

Phe Leu Pro Asp Gln Met Gln Pro Gln Val Pro Pro Leu His Tyr Gln
        355                 360                 365

Glu Leu Met Pro Pro Gly Ser Cys Met Pro Glu Pro Lys Pro Lys
    370                 375                 380

Arg Gly Arg Arg Ser Trp Pro Arg Lys Arg Thr Ala Thr His Thr Cys
385                 390                 395                 400

Asp Tyr Ala Gly Cys Gly Lys Thr Tyr Thr Lys Ser Ser His Leu Lys
```

-continued

```
                       405                 410                 415
Ala His Leu Arg Thr His Thr Gly Glu Lys Pro Tyr His Cys Asp Trp
            420                 425                 430

Asp Gly Cys Gly Trp Lys Phe Ala Arg Ser Asp Glu Leu Thr Arg His
                435                 440                 445

Tyr Arg Lys His Thr Gly His Arg Pro Phe Gln Cys Gln Lys Cys Asp
            450                 455                 460

Arg Ala Phe Ser Arg Ser Asp His Leu Ala Leu His Met Lys Arg His
465                 470                 475                 480

Phe

<210> SEQ ID NO 7
<211> LENGTH: 1320
<212> TYPE: DNA
<213> ORGANISM: Canis lupus
<220> FEATURE:
<221> NAME/KEY: CDS
<222> LOCATION: (1)..(1320)

<400> SEQUENCE: 7 atg cct ctc aac gta agc ttc gcc aat agg aac tat gac ctc gac tac      48
Met Pro Leu Asn Val Ser Phe Ala Asn Arg Asn Tyr Asp Leu Asp Tyr
1               5                   10                  15 gac tcg gtg cag ccg tat ttc tac tgc gac gag gag gag aac ttc tac      96
Asp Ser Val Gln Pro Tyr Phe Tyr Cys Asp Glu Glu Glu Asn Phe Tyr
                20                  25                  30 cag cag cag cag cag agc gag ctg cag ccg ccg gcg ccc agc gag gat     144
Gln Gln Gln Gln Gln Ser Glu Leu Gln Pro Pro Ala Pro Ser Glu Asp
            35                  40                  45 atc tgg aag aaa ttc gag ctg ctg ccc acc ccg ccg ctg tcc ccg agc     192
Ile Trp Lys Lys Phe Glu Leu Leu Pro Thr Pro Pro Leu Ser Pro Ser
        50                  55                  60 cgc cgc tcc ggg ctc tgc tcg ccc tcc tac gtc gca gtc gcg tcc ttc     240
Arg Arg Ser Gly Leu Cys Ser Pro Ser Tyr Val Ala Val Ala Ser Phe
65                  70                  75                  80 tcc ccc cgg ggg gac gat gac ggc ggc ggc ggc agc ttc tcc acc gcc     288
Ser Pro Arg Gly Asp Asp Asp Gly Gly Gly Gly Ser Phe Ser Thr Ala
                85                  90                  95 gac cag ttg gag atg gtg acc gag ctg ctg gga gga gac atg gtg aac     336
Asp Gln Leu Glu Met Val Thr Glu Leu Leu Gly Gly Asp Met Val Asn
            100                 105                 110 cag agc ttc atc tgc gac ccg gac gac gag acc ttc atc aaa aac atc     384
Gln Ser Phe Ile Cys Asp Pro Asp Asp Glu Thr Phe Ile Lys Asn Ile
        115                 120                 125 atc atc cag gac tgc atg tgg agc ggc ttc tcg gcc gcc gcc aag ctc     432
Ile Ile Gln Asp Cys Met Trp Ser Gly Phe Ser Ala Ala Ala Lys Leu
    130                 135                 140 gtc tcg gag aag ctg gcc tcc tac cag gct gcg cgc aaa gac agc ggc     480
Val Ser Glu Lys Leu Ala Ser Tyr Gln Ala Ala Arg Lys Asp Ser Gly
145                 150                 155                 160 agc ccg agc ccc gcc cgc ggg ccc ggc ggc tgc tcc acc tcc agc ctg     528
Ser Pro Ser Pro Ala Arg Gly Pro Gly Gly Cys Ser Thr Ser Ser Leu
                165                 170                 175 tac ctg cag gac ctg agc gcc gcc gcc tcc gag tgc atc gac ccc tcc     576
Tyr Leu Gln Asp Leu Ser Ala Ala Ala Ser Glu Cys Ile Asp Pro Ser
            180                 185                 190 gtg gtc ttc ccc tac ccg ctc aat gac agc agc tcg ccc aag ccc tgc     624
Val Val Phe Pro Tyr Pro Leu Asn Asp Ser Ser Ser Pro Lys Pro Cys
        195                 200                 205 gcg tcc ccc gac tcg gcc gcc ttc tcc ccg tcc tcg gac tct ctg ctc     672
```

```
                                          -continued
Ala Ser Pro Asp Ser Ala Ala Phe Ser Pro Ser Ser Asp Ser Leu Leu
        210                 215                 220 tcc tcg gcc gag tcc tcc ccc cgg gcc agc ccc gag ccc ctg gcg ctg       720
Ser Ser Ala Glu Ser Ser Pro Arg Ala Ser Pro Glu Pro Leu Ala Leu
225                 230                 235                 240 cac gag gag aca ccg ccc acc acc agc agc gac tcg gag gaa gaa caa       768
His Glu Glu Thr Pro Pro Thr Thr Ser Ser Asp Ser Glu Glu Glu Gln
                245                 250                 255 gag gac gaa gaa gaa att gat gtt gtt tct gtg gaa aaa agg cag ccc       816
Glu Asp Glu Glu Glu Ile Asp Val Val Ser Val Glu Lys Arg Gln Pro
            260                 265                 270 cct gcc aaa agg tcc gaa tcg ggg tcc ccc tct gct gga ggc cac agc       864
Pro Ala Lys Arg Ser Glu Ser Gly Ser Pro Ser Ala Gly Gly His Ser
        275                 280                 285 aaa cct cct cac agc ccg ctg gtc ctt aag aga tgc cat gtg tcc acc       912
Lys Pro Pro His Ser Pro Leu Val Leu Lys Arg Cys His Val Ser Thr
290                 295                 300 cat cag cac aac tac gcg gca ccc ccc tcc acc agg aag gac tat ccc       960
His Gln His Asn Tyr Ala Ala Pro Pro Ser Thr Arg Lys Asp Tyr Pro
305                 310                 315                 320 gcc gcc aag agg gcg agg ttg gac agt ggt aga gtc ctg aaa cag atc      1008
Ala Ala Lys Arg Ala Arg Leu Asp Ser Gly Arg Val Leu Lys Gln Ile
                325                 330                 335 agc aac aac cgc aaa tgt gcc agc ccc agg tct tcg gac acg gag gag      1056
Ser Asn Asn Arg Lys Cys Ala Ser Pro Arg Ser Ser Asp Thr Glu Glu
            340                 345                 350 aat gac aag agg cga aca cac aac gtc ttg gag cgc cag agg agg aac      1104
Asn Asp Lys Arg Arg Thr His Asn Val Leu Glu Arg Gln Arg Arg Asn
        355                 360                 365 gag ctg aaa cgg agc ttc ttt gcc ctg cgt gat cag atc ccg gag ttg      1152
Glu Leu Lys Arg Ser Phe Phe Ala Leu Arg Asp Gln Ile Pro Glu Leu
370                 375                 380 gaa aac aat gaa aag gcc ccc aag gta gtg atc ctt aaa aaa gcc acc      1200
Glu Asn Asn Glu Lys Ala Pro Lys Val Val Ile Leu Lys Lys Ala Thr
385                 390                 395                 400 gcg tac atc ctg tcc gtc caa gcc gag gag caa aag ctc ctt tcc gaa      1248
Ala Tyr Ile Leu Ser Val Gln Ala Glu Glu Gln Lys Leu Leu Ser Glu
                405                 410                 415 aag gac ttg ttg cgg aag cgg cga gaa cag ttg aaa cac aaa ctg gaa      1296
Lys Asp Leu Leu Arg Lys Arg Arg Glu Gln Leu Lys His Lys Leu Glu
            420                 425                 430 cag cta agg aac tct ggt gcc taa                                      1320
Gln Leu Arg Asn Ser Gly Ala
        435

<210> SEQ ID NO 8
<211> LENGTH: 439
<212> TYPE: PRT
<213> ORGANISM: Canis lupus

<400> SEQUENCE: 8

Met Pro Leu Asn Val Ser Phe Ala Asn Arg Asn Tyr Asp Leu Asp Tyr
1               5                   10                  15

Asp Ser Val Gln Pro Tyr Phe Tyr Cys Asp Glu Glu Asn Phe Tyr
                20                  25                  30

Gln Gln Gln Gln Gln Ser Glu Leu Gln Pro Pro Ala Pro Ser Glu Asp
            35                  40                  45

Ile Trp Lys Lys Phe Glu Leu Leu Pro Thr Pro Pro Leu Ser Pro Ser
        50                  55                  60

Arg Arg Ser Gly Leu Cys Ser Pro Ser Tyr Val Ala Val Ala Ser Phe
```

```
                65                  70                  75                  80
Ser Pro Arg Gly Asp Asp Gly Gly Gly Ser Phe Ser Thr Ala
                        85                  90                  95
Asp Gln Leu Glu Met Val Thr Glu Leu Leu Gly Gly Asp Met Val Asn
                100                 105                 110
Gln Ser Phe Ile Cys Asp Pro Asp Glu Thr Phe Ile Lys Asn Ile
            115                 120                 125
Ile Ile Gln Asp Cys Met Trp Ser Gly Phe Ser Ala Ala Ala Lys Leu
        130                 135                 140
Val Ser Glu Lys Leu Ala Ser Tyr Gln Ala Ala Arg Lys Asp Ser Gly
145                 150                 155                 160
Ser Pro Ser Pro Ala Arg Gly Pro Gly Gly Cys Ser Thr Ser Ser Leu
                165                 170                 175
Tyr Leu Gln Asp Leu Ser Ala Ala Ser Glu Cys Ile Asp Pro Ser
            180                 185                 190
Val Val Phe Pro Tyr Pro Leu Asn Asp Ser Ser Pro Lys Pro Cys
        195                 200                 205
Ala Ser Pro Asp Ser Ala Ala Phe Ser Pro Ser Ser Asp Ser Leu Leu
    210                 215                 220
Ser Ser Ala Glu Ser Ser Pro Arg Ala Ser Pro Glu Pro Leu Ala Leu
225                 230                 235                 240
His Glu Glu Thr Pro Pro Thr Thr Ser Ser Asp Ser Glu Glu Glu Gln
                245                 250                 255
Glu Asp Glu Glu Glu Ile Asp Val Val Ser Val Glu Lys Arg Gln Pro
                260                 265                 270
Pro Ala Lys Arg Ser Glu Ser Gly Ser Pro Ser Ala Gly Gly His Ser
            275                 280                 285
Lys Pro Pro His Ser Pro Leu Val Leu Lys Arg Cys His Val Ser Thr
        290                 295                 300
His Gln His Asn Tyr Ala Ala Pro Pro Ser Thr Arg Lys Asp Tyr Pro
305                 310                 315                 320
Ala Ala Lys Arg Ala Arg Leu Asp Ser Gly Arg Val Leu Lys Gln Ile
                325                 330                 335
Ser Asn Asn Arg Lys Cys Ala Ser Pro Arg Ser Ser Asp Thr Glu Glu
                340                 345                 350
Asn Asp Lys Arg Arg Thr His Asn Val Leu Glu Arg Gln Arg Arg Asn
            355                 360                 365
Glu Leu Lys Arg Ser Phe Phe Ala Leu Arg Asp Gln Ile Pro Glu Leu
        370                 375                 380
Glu Asn Asn Glu Lys Ala Pro Lys Val Val Ile Leu Lys Lys Ala Thr
385                 390                 395                 400
Ala Tyr Ile Leu Ser Val Gln Ala Glu Glu Gln Lys Leu Leu Ser Glu
                405                 410                 415
Lys Asp Leu Leu Arg Lys Arg Glu Gln Leu Lys His Lys Leu Glu
            420                 425                 430
Gln Leu Arg Asn Ser Gly Ala
        435

<210> SEQ ID NO 9
<211> LENGTH: 40
<212> TYPE: DNA
<213> ORGANISM: Artificial Sequence
<220> FEATURE:
<223> OTHER INFORMATION: Primer

<400> SEQUENCE: 9
```

-continued ttaattaagg atccaccatg gctgtcagcg acgctctgct            40

<210> SEQ ID NO 10
<211> LENGTH: 42
<212> TYPE: DNA
<213> ORGANISM: Artificial Sequence
<220> FEATURE:
<223> OTHER INFORMATION: Primer

<400> SEQUENCE: 10
ggcctgcagg aattcttaaa agtgcctctt catgtgtaag gc            42

<210> SEQ ID NO 11
<211> LENGTH: 40
<212> TYPE: DNA
<213> ORGANISM: Artificial Sequence
<220> FEATURE:
<223> OTHER INFORMATION: Primer

<400> SEQUENCE: 11
ttaattaagg atccaccatg gcgggacacc tggcttccga            40

<210> SEQ ID NO 12
<211> LENGTH: 40
<212> TYPE: DNA
<213> ORGANISM: Artificial Sequence
<220> FEATURE:
<223> OTHER INFORMATION: Primer

<400> SEQUENCE: 12
ggcctgcagg aattctcaat ttgaatgcat gggagagccc            40

<210> SEQ ID NO 13
<211> LENGTH: 24
<212> TYPE: DNA
<213> ORGANISM: Artificial Sequence
<220> FEATURE:
<223> OTHER INFORMATION: Primer

<400> SEQUENCE: 13
atgtacaaca tgatggagac ggag            24

<210> SEQ ID NO 14
<211> LENGTH: 24
<212> TYPE: DNA
<213> ORGANISM: Artificial Sequence
<220> FEATURE:
<223> OTHER INFORMATION: Primer

<400> SEQUENCE: 14
tcacatgtgc gagaggggca gtgt            24

<210> SEQ ID NO 15
<211> LENGTH: 40
<212> TYPE: DNA
<213> ORGANISM: Artificial Sequence
<220> FEATURE:
<223> OTHER INFORMATION: Primer

<400> SEQUENCE: 15
ttaattaagg atccaccctg gatctcctcc ggagagtgga            40

<210> SEQ ID NO 16
<211> LENGTH: 40
<212> TYPE: DNA
<213> ORGANISM: Artificial Sequence

```
<220> FEATURE:
<223> OTHER INFORMATION: Primer

<400> SEQUENCE: 16
ggcctgcagg aattcttagg caccagagtt ccttagctgt                             40

<210> SEQ ID NO 17
<211> LENGTH: 21
<212> TYPE: DNA
<213> ORGANISM: Artificial Sequence
<220> FEATURE:
<223> OTHER INFORMATION: Primer

<400> SEQUENCE: 17
ggctccagta tataaatcag g                                                 21

<210> SEQ ID NO 18
<211> LENGTH: 21
<212> TYPE: DNA
<213> ORGANISM: Artificial Sequence
<220> FEATURE:
<223> OTHER INFORMATION: Primer

<400> SEQUENCE: 18
aaactgccgg catctaaggt c                                                 21

<210> SEQ ID NO 19
<211> LENGTH: 29
<212> TYPE: DNA
<213> ORGANISM: Artificial Sequence
<220> FEATURE:
<223> OTHER INFORMATION: Primer

<400> SEQUENCE: 19
ctagaaggcc tgggccacca cggcaatga                                         29

<210> SEQ ID NO 20
<211> LENGTH: 24
<212> TYPE: DNA
<213> ORGANISM: Artificial Sequence
<220> FEATURE:
<223> OTHER INFORMATION: Primer

<400> SEQUENCE: 20
cccagctgta tgttctcaat gatc                                              24

<210> SEQ ID NO 21
<211> LENGTH: 22
<212> TYPE: DNA
<213> ORGANISM: Artificial Sequence
<220> FEATURE:
<223> OTHER INFORMATION: Primer

<400> SEQUENCE: 21
tcttgcatct gctggagact ga                                                22

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
tcgtccatgg tcctcgagat                                                   20
```

```
<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
agtttcgcac gctcattgaa                                              20
```

US 8,709,805 B2

CANINE IPS CELLS AND METHOD OF PRODUCING SAME

CROSS-REFERENCE TO RELATED APPLICATION

This application claims the benefit of Japanese Patent Application No. 2009-185268 filed Aug. 7, 2009, the content of which is incorporated herein by reference.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 41,157 bytes ASCII (Text) file named "706794SequenceListing.txt," created Aug. 5, 2010.

FIELD OF THE INVENTION

The present invention relates to a method of producing a canine iPS cell, specifically to a method of producing a canine iPS cell by transferring a nuclear reprogramming factor to a canine somatic cell, and culturing the cell in a medium containing a defined reprogramming efficiency improver. The present invention also relates to canine iPS cells transfected with the nuclear reprogramming factor.

BACKGROUND OF THE INVENTION

An induced pluripotent stem (iPS) cell is a cell generated by transferring a defined nuclear reprogramming factor to a somatic cell to confer pluripotency to the somatic cell. The term pluripotency refers to the potential for differentiating into a wide variety of tissues; it is believed that tissue degenerative diseases such as Parkinson's disease and juvenile diabetes, as well as traumas such as spinal injuries, can be treated by using this property.

Traditionally, ES cells (embryonic stem cells), which likewise possess pluripotency, have been attracting attention as a resource for regenerative medicine. However, ES cell transplantation can cause graft rejection because it is a form of allotransplantation, and has been viewed as posing ethical problems, including destructive use of human embryos and employment of abortive fetuses. In contrast, iPS cells, which are generated using somatic cells, can be thought to have resolved these problems, and are expected to be highly useful as a resource for regenerative medicine in the future.

As such, iPS cells have been established mainly in mice and humans (see patent documents 1-2, and non-patent documents 1-3). Human IFS cells cannot be applied clinically until their safety and efficacy are previously assured by animal experimentation. However, small animals, such as mice and rats, do not permit long-term follow-up examination after undergoing cell transplantation because of their short longevity. While it seems ideal that at least 5 years be secured for the examination, the longevity of the mouse is up to 1 to 2 years.

Meanwhile, the dog is a laboratory animal that can easily be handled, lives long, and is similar to humans in many features, both anatomically and physiologically. The longevity of the dog is at least 10 years, sufficient for a length of follow-up examination. The dog also permits easier mass-breeding than other large animals. For this reason, the dog is the laboratory animal best suited for determining the clinical applicability of human IFS cells; the experimental results obtained by transplantation of IFS cells to dogs are believed to be highly useful. To this end, it is necessary to generate a canine iPS cell; however, no reports are available on actual establishment thereof.

patent document 1: WO 2007/069666
patent document 2: WO 2008/118820
non-patent document 1: Takahashi, K. et al., *Cell,* 126(4): 663-676 (2006)
non-patent document 2: Takahashi, K. et al., *Cell,* 131: 861-872 (2007)
non-patent document 3: Yu, J. et al., *Science,* 318: 1917-1920 (2007)

SUMMARY OF THE INVENTION

The present invention is directed to providing canine iPS cells and a method of producing the same.

Means of Solving the Problems

The present inventors extensively investigated to solve the above-described problems, focused on culturing conditions after transfer of nuclear reprogramming factors and found that out of various compound ingredients of the medium composition, especially, mitogen-activated protein kinase kinase inhibitors, activin receptor-like kinase inhibitors and glycogen synthase kinase inhibitors, or L-type calcium channel agonists and DNA methylation inhibitors, and leukemia inhibitory factors (LIFs) are effective in producing canine iPS cells. The inventors conducted further investigations based on this finding, and succeeded for the first time in establishing a canine iPS cell by culturing a somatic cell transfected with a nuclear reprogramming factor, using a medium containing the components, and have developed the present invention.

Accordingly, the present invention provides the following:
[1] A method of producing a canine iPS cell, comprising the steps (a) and (b) below:
(a) the step of bringing into contact with each other a canine somatic cell and a nuclear reprogramming factor,
(b) the step of culturing the cell in a medium containing one or more substance(s) selected from the group consisting of a mitogen-activated protein kinase kinase inhibitor, an activin receptor-like kinase inhibitor, a glycogen synthase kinase inhibitor, a L-type calcium channel agonist and a DNA methylation inhibitor, and a leukemia inhibitory factor.
[2] The process according to [1] above, wherein the more than one substances are a mitogen-activated protein kinase kinase inhibitor and a glycogen synthase kinase inhibitor; a mitogen-activated protein kinase kinase inhibitor, an activin receptor-like kinase inhibitor and a glycogen synthase kinase inhibitor; or a L-type calcium channel agonist and a DNA methylation inhibitor.
[3] The process according to [1] or [2] above, wherein the nuclear reprogramming factor is Oct3/4, Sox2 and Klf4.
[4] The process according to [1] or [2] above, wherein the nuclear reprogramming factor is Oct3/4, Sox2, Klf4 and c-Myc.
[5] The process according to any one of [1] to [4] above, wherein the activin receptor-like kinase inhibitor is an activin receptor-like kinase 5 inhibitor.
[6] The process according to any one of [1] to [5] above, wherein the glycogen synthase kinase inhibitor is a glycogen synthase kinase 3β inhibitor.
[7] The process according to any one of [1] to [6] above, wherein the medium for the step (b) further contains a histone deacetylase inhibitor.
[8] The process according to [7] above, wherein the histone deacetylase inhibitor is valproic acid or a salt thereof.

[9] The process according to any one of [1] to [8] above, wherein the medium for the step (b) further contains a basic fibroblast growth factor.
[10] The process according to any one of [1] to [9] above, wherein the cultivation in the step (b) is performed within 48 hours after contact with the nuclear reprogramming factor.
[11] The process according to any one of [1] to [10] above, wherein the cultivation is performed on feeder cells after the elapse of 3 to 5 weeks after contact with the nuclear reprogramming factor.
[12] The process according to any one of [1] to [11] above, wherein the leukemia inhibitory factor is a human or canine leukemia inhibitory factor.
[13] The process according to any one of [1] to [12] above, wherein the somatic cell is an adipose-derived cell.
[14] A canine pluripotent stem cell of somatic cell derivation possessing pluripotency and a potential for self-replication.
[15] The cell according to [14] above, wherein the reprogramming gene is genetically stably present.
[16] The cell according to [15] above, wherein the reprogramming gene is at least one selected from among Oct3/4, Sox2, Klf4 and c-Myc.
[17] A canine iPS cell produced by the process according to any one of [1] to [13] above.
[18] A canine somatic cell differentiated from the cell according to any one of [14] to [17] above.

According to the present invention, canine iPS cells can be stably produced from canine somatic cells and can be provided by using the method of production thereof, whereby long-term follow-up examination after cell or tissue transplantation in animal experiments is possible before clinically applying human iPS cells, and the results obtained by the experiments are effectively utilizable.

Additionally, production of canine iPS cells from each individual by the present invention would radically revolutionize currently available therapies in veterinary medicine, making tailor-made treatment of diseased dogs possible. Furthermore, utilizing canine iPS cells according to the present invention will make it possible to develop veterinary drugs, and to test chemical substances for their toxicity, without using individual dogs.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Panels (a) and (b) in FIG. 1 show results of electrophoresis of canine Klf4, Oct3/4, c-Myc, and Sox2 amplified by PCR on the basis of total RNAs extracted from canine tissues (cerebrum, retina, gastric mucosa, skin, skeletal muscle, lung, testis). Panel (c) shows the pMXs-IRES-GFP vector incorporating the individual genes.

FIG. 3 shows the efficiency of gene transfer to canine fibroblasts. The canine fibroblasts were infected with a retrovirus bearing a cDNA of GFP to transfer the GFP. Panel (a) is a graphic representation of flow cytometry results; panel (b) shows a fluorescent photomicrograph.

FIG. 4 shows observations of cell morphological changes and GFP expression rates after transfection, wherein panels (a) and (b) show photomicrographs taken on day 2 after transfection, and panels (c) and (d) show photomicrographs taken on day 5 after transfection.

FIG. 5 compares cell morphological changes observed before and after transfection, wherein panel (a) shows the morphology of cells before transfection, and panel (b) shows the morphology of cells on day 5 after transfection. Panel (c) shows colonies observed on day 30 after transfection, and panel (d) is a magnified view of (c).

FIG. 6-1 shows analytical results obtained by immunohistological staining. Panels (a) and (c) show the expression Oct3/4 and SSEA-1 as ES cell markers, respectively. Panels (b) and (d) show the results of nuclear staining (double staining) of the cells shown in panels (a) and (c), respectively, with DAPI.

FIG. 6-2, like FIG. 6-1, shows analytical results obtained by immunohistological staining. Panels (e), (g) and (i) show the expression of SSEA-4, TRA-1-60, and TRA-1-81, as ES cell markers, respectively. Panels (f), (h), and (j) show the results of nuclear staining (double staining) of the cells shown in panels (e), (g), and (i), respectively, with DAPI.

FIG. 7 shows results of alkaline phosphatase staining of canine iPS cells generated from a canine fibroblast, wherein panel (a) shows the results for a canine iPS cell, and panel (b) for a mouse iPS cell.

FIG. 8 shows the potential of differentiation induction of canine iPS cells. Panels (a), (c), and (e) show the expression of AFP (α-fetoprotein), FLK1, and βIII tubulin, as differentiation induction markers, respectively. Panels (b), (d), and (f) show the results of nuclear staining (double staining) of the cells shown in (a), (c), and (e), respectively, with DAPI.

FIG. 13 is a photomicrograph of a colony of canine iPS cells (right panel) established from adipose-derived cells (left panel).

DETAILED DESCRIPTION OF THE INVENTION

Figure 2:
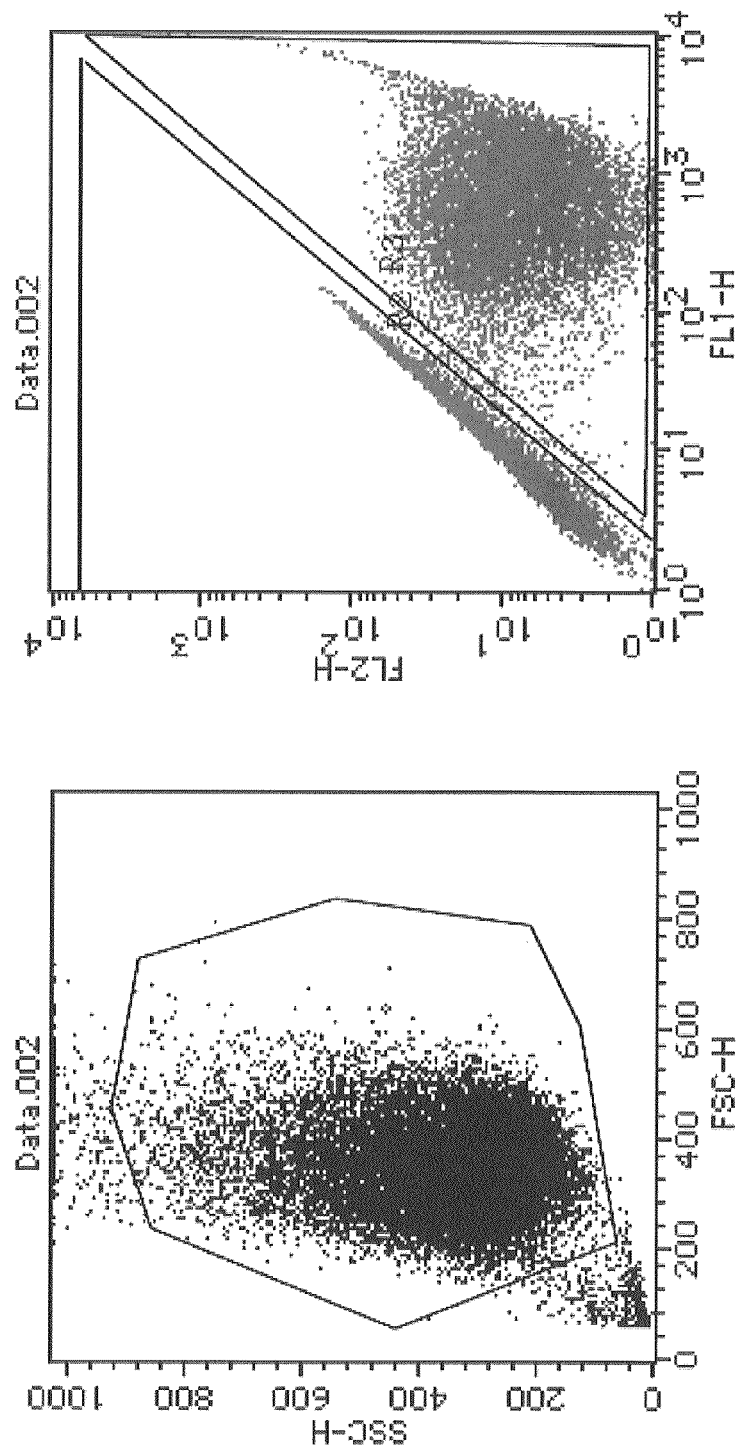
FIG. 2 is a graphic representation of the efficiency of gene transfer to canine fibroblasts, wherein the axis of ordinates indicates forward scattered light (size), and the axis of abscissas indicates lateral scattered light (internal structure). Expression of the GFP gene is seen in 50 to 60% of all cells.

The present invention is hereinafter described in detail.

The present invention provides a method of producing a canine iPS cell, comprising (a) the step of transferring a nuclear reprogramming factor to a canine somatic cell, and (b) the step of culturing the somatic cell incorporating the nuclear reprogramming factor using a medium containing at least one substance selected from the group consisting of a mitogen-activated protein kinase kinase inhibitor, an activin receptor-like kinase inhibitor, a glycogen synthase kinase inhibitor, a L-type calcium channel agonist, and a DNA methylation inhibitor, and a leukemia inhibitory factor.

A nuclear reprogramming factor in the present invention is a factor that induces nuclear reprogramming in a canine somatic cell, being a substance capable of conferring pluripotency and a potential for self-replication to the canine somatic cell to convert the somatic cell into a canine iPS cell. The choice of nuclear reprogramming factor is not particularly limited; for example, nucleic acids (genes), peptides, proteins, organic compounds, inorganic compounds or mixtures thereof and the like can be used. When the nuclear reprogramming factor is a proteinous factor or a nucleic acid that encodes the same, it is preferably a transcription factor from the viewpoint of activating the signal transduction pathway that promotes the nuclear reprogramming of canine somatic cells. Of the transcription factors, specifically, the combination of 4 factors consisting of Oct3/4, Sox2, Klf4 and c-Myc is particularly preferable. Bearing in mind the use of the canine iPS cell thus obtained for transplantation medicine in dogs, the combination of 3 factors consisting of Oct3/4, Sox2 and Klf4, but not including c-Myc, is more preferable for the sake of reducing the risk of carcinogenesis. Combinations containing all of the aforementioned 4 factors or 3 factors, and further containing an optionally chosen other factor, can also be encompassed in preferred modes of nuclear reprogramming factors in the present invention. Provided that the somatic cell to undergo nuclear reprogramming is endogenously expressing some of the aforementioned 4 factors at a level sufficient to allow the nuclear reprogramming, the combination of the remaining factors only, excluding the endogenously expressed factor(s), can also be encompassed in preferred modes of nuclear reprogramming factors in the present invention. Nuclear reprogramming factors include factors other than the aforementioned 4 factors. Specifically, such other factors include Nanog, Lin28, TERT, SV40 large T antigen and the like.

Oct3/4 is exemplified by canine Oct3/4 shown by SEQ ID NO:1 and 2, and Oct3/4 derived from other mammals (e.g., mouse Oct3/4, human Oct3/4). Sox2 is exemplified by canine Sox2 shown by SEQ ID NO:3 and 4, and Sox2 derived from other mammals (e.g., mouse Sox2, human Sox2). Klf4 is exemplified by canine Klf4 shown by SEQ ID NO:5 and 6, and Klf4 derived from other mammals (e.g., mouse Klf4, human Klf4). c-Myc is exemplified by canine c-Myc shown by SEQ ID NO:7 and 8, and c-Myc derived from other mammals (e.g., mouse c-Myc, human c-Myc). The amino acid sequences of the aforementioned 4 factors of mouse and human derivation and the nucleotide sequences of cDNAs thereof can be acquired by referring to the NCBI accession numbers shown in WO2007/069666.

The 4 factors may be ones of extremely high homology having an amino acid sequence resulting from deletion, substitution, insertion or addition of one or several (2 to 5) amino acids in one of the foregoing amino acid sequences, or the base sequence that encodes the amino acid sequence, as far as they allow the production of a canine iPS cell when transferred to a canine somatic cell.

Here, a gene "of extremely high homology" means a gene that hybridizes with a nucleic acid that encodes one of the 4 factors under stringent conditions, specifically a gene having an identity of 70% or more, preferably 80% or more, more preferably 90% or more, particularly preferably 95% or more, to the 4 factors shown by the foregoing sequence identification numbers.

Although the choice of dog variety for collection of canine somatic cells in the present invention is not particularly limited, varieties in common use for experimental purposes, for example, beagle, basset hound, foxhound, Scottish terrier, Labrador retriever and the like, are useful when the canine iPS cell obtained is to be used for research purposes. The choice of somatic cell is also not particularly limited, as far as an iPS cell is produced by transferring a nuclear reprogramming factor; an optionally chosen canine somatic cell can be used. For example, in addition to fetal somatic cells, mature somatic cells can also be used. Specifically, tissue stem cells (somatic stem cells) such as adipose-derived stromal (stem) cells, nervous stem cells, hematopoietic stem cells, mesenchymal stem cells, and spermatozoon stem cells; tissue progenitor cells; differentiated cells such as lymphocytes, epidermal cells, muscle cells, and fibroblasts, and the like can be used. From the perspective of high establishment efficiency of iPS cells, in one preferable embodiment, a cell population containing adipose-derived stromal (stem) cells as somatic cells can be used.

To facilitate the selection of iPS cells, it is possible to use, for example, a recombinant somatic cell wherein a drug resistance gene (e.g., neomycin resistance gene, puromycin resistance gene) and/or a reporter gene (e.g., β-galactosidase gene, green fluorescent protein (GFP) gene) has been targeted to the locus of a gene highly expressed specifically in pluripotent cells (e.g., Fbx15, Nanog, Oct3/4 and the like).

The choice of dog individual as a source of somatic cells is not particularly limited; however, when the iPS cells obtained are to be used for regenerative medicine in dogs, it is preferable, from the viewpoint of prevention of graft rejection, that somatic cells are animal's own cells or collected from another animal having the same or substantially the same MHC type as that of the patient. "Substantially the same MHC type" as used herein means that the MHC type of donor matches with that of animal to the extent that the transplanted cells, which have been obtained by inducing differentiation of iPS cells derived from the donor's somatic cells, can be engrafted when they are transplanted to the patient with use of immunosuppressor and the like.

Somatic cells isolated from a dog can be pre-cultured using a medium known per se suitable for their cultivation according to the choice of cells. Examples of such media include, but are not limited to, minimal essential medium (MEM) containing about 5 to 20% fetal calf serum, Dulbecco's modified Eagle medium (DMEM), RPMI1640 medium, 199 medium, F12 medium, and the like.

The procedure for transferring a nuclear reprogramming factor to a canine somatic cell in the step (a) of the present invention is not particularly limited; any method is acceptable, as far as it allows the nuclear reprogramming factor to come in contact with the canine somatic cell. For example, provided that the nuclear reprogramming factor of the present invention is a nucleic acid that encodes a transcription factor or the like, the nuclear reprogramming factor can be transferred to the canine somatic cell using a vector capable of expressing the nucleic acid. When using such a vector, and provided that two or more different nucleic acids are the nuclear reprogramming factors of the present invention, the two or more different nucleic acids may be integrated in a single vector and allowed to be simultaneously expressed in the canine somatic cell; alternatively, the two or more different nucleic acids may be expressed using a plurality of vectors. In the former case, to allow efficient polycistronic expression, it is desirable that the 2A self-cleaving peptide of foot-and-mouth disease virus [see *Science*, 322, 949-953 (2008) and the like] or IRES be inserted between the nucleic acids.

The choice of vector capable of expressing a gene is not particularly limited; examples include viral vectors such as retroviruses (including lentivirus), adenovirus, adeno-associated virus, Sendai virus, herpesvirus, vaccinia virus, poxvirus, poliovirus, sindbis virus, rhabdovirus, paramyxovirus, and orthomyxovirus; artificial chromosome vectors such as YAC (Yeast artificial chromosome) vector, BAC (Bacterial artificial chromosome) vector, and PAC (P1-derived artificial chromosome) vector; plasmid vectors; episomal vectors capable of self-replication in the host cell, and the like. When the vector is transferred to the canine somatic cell of the present invention, known methods such as lipofection, microinjection, the DEAE dextran method, the gene gun method, electroporation, the calcium phosphate method and the like can be used.

When the vector used is a viral vector, a packaging cell can be utilized. A packaging cell refers to a cell transfected with a gene that encodes a structural protein of a virus, wherein transfection with a recombinant virus DNA incorporating a target gene causes the cell to produce particles of the recombinant virus. For this reason, any packaging cells can be used, as far as it supplements a protein necessary for the constitution of the virus particle for the recombinant viral vector; for example, packaging cells based on human renal HEK293 cell or mouse fibroblast NIH3T3 cell; Plat-E cell designed to express an Ecotropic virus-derived envelop glycoprotein, Plat-A cell designed to express an Amphotropic virus-derived envelop glycoprotein, and Plat-GP cell designed to express a vesicular stomatitis virus-derived envelop glycoprotein, and the like can be used (Plat-E cell, Plat-A cell and Plat-GP cell can be purchased from CELL BIOLABS). In particular, when a recombinant viral vector is transferred to the canine somatic cell of the present invention, Plat-A cell or Plat-GP cell is preferred, with greater preference given to Plat-GP cell. The method of transferring a viral vector to the packaging cell is not particularly limited; conventionally known methods such as lipofection, electroporation and the calcium phosphate method can be utilized.

When a gene is transferred using the vector, a marker gene can also be utilized at the same time in order to confirm the transfer of the gene. A marker gene generically refers to a gene that enables cell sorting or selection when transferred to cells; examples include drug resistance genes, fluorescent protein genes, luminescent enzyme genes, color developing enzyme genes and the like. Drug resistance genes include the neomycin resistance gene, tetracycline resistance gene, kanamycin resistance gene, zeosin resistance gene, hygromycin resistance gene and the like; fluorescent protein genes, include the green fluorescent protein (GFP) gene, yellow fluorescent protein (YFP) gene, red fluorescent protein (RFP) gene and the like. Luminescent enzyme genes include the luciferase gene and the like; color-developing enzyme genes include the β-galactosidase gene, β-glucuronidase gene, alkaline phosphatase gene and the like. These marker genes can be used singly or in combination of two or more kinds. A fusion gene containing two or more marker genes, like the βgeo gene, which is a fusion gene of the neomycin resistance gene and the β-galactosidase gene, can also be used.

The nuclear reprogramming factor transferring operation can be performed one or more optionally chosen times (e.g., once or more to 10 times or less, or once or more to 5 times or less and the like). Preferably, the transferring operation can be performed twice or more (e.g., 3 times or 4 times) repeatedly. The time interval for repeated transferring operation is, for example, 6 to 48 hours, preferably 12 to 24 hours.

Meanwhile, when the nuclear reprogramming factor is a proteinous factor such as a transcription factor, contact of the canine somatic cell and nuclear reprogramming factor can be achieved using a method of protein transfer known per se. The protein transferring operation can be performed one or more optionally chosen times (e.g., once or more to 10 times or less, or once or more to 5 times or less and the like). Preferably, the transferring operation can be performed twice or more (e.g., 3 times or 4 times) repeatedly. The time interval for repeated transferring operation is, for example, 6 to 48 hours, preferably 12 to 24 hours.

In view of clinical applications to dogs, it is preferable that the iPS cell be prepared without gene manipulation.

Such methods include, for example, the method using a protein transfer reagent, the method using a protein transfer domain (PTD)- or cell penetrating peptide (CPP)-fusion protein, the microinjection method and the like. Protein transfer reagents are commercially available, including those based on a cationic lipid, such as BioPOTER Protein Delivery Reagent (Gene Therapy Systems), Pro-Ject™ Protein Transfection Reagent (PIERCE) and ProVectin (IMGENEX); those based on a lipid, such as Profect-1 (Targeting Systems); those based on a membrane-permeable peptide, such as Penetrain Peptide (Q biogene) and Chariot Kit (Active Motif), GenomONE (ISHIHARA SANGYO KAISHA, LTD.) utilizing HVJ envelope (inactivated hemagglutinating virus of Japan) and the like. The transfer can be achieved per the protocols attached to these reagents, a common procedure being as described below. Nuclear reprogramming factor(s) is(are) diluted in an appropriate solvent (e.g., a buffer solution such as PBS or HEPES), a transfer reagent is added, the mixture is incubated at room temperature for about 5 to 15 minutes to form a complex, this complex is added to cells after exchanging the medium with a serum-free medium, and the cells are incubated at 37° C. for one to several hours. Thereafter, the medium is removed and replaced with a serum-containing medium.

Developed PTDs include those using transcellular domains of proteins such as *drosophila*-derived AntP, HIV-derived TAT, HSV-derived VP22 and the like. CPPs derived from the PTDs include polyarginines such as 11R [*Cell Stem Cell*, 4, 381-384 (2009)] and 9R [*Cell Stem Cell*, 4, 472-476 (2009)]. A fused protein expression vector incorporating cDNA of a nuclear reprogramming factor and PTD or CPP sequence is prepared, and recombination expression is performed using the vector. The fused protein is recovered and used for transfer. Transfer can be performed in the same manner as above except that a protein transfer reagent is not added.

Microinjection, a method of placing a protein solution in a glass needle having a tip diameter of about 1 μm, and injecting the solution into a cell, ensures the transfer of the protein into the cell.

After being contacted with the nuclear reprogramming factor, the canine somatic cell is subjected to the step (b) using a medium for iPS cell induction at an appropriate time. The medium in the step (b) of the present invention contains at least one of a mitogen-activated protein kinase kinase inhibitor, an activin receptor-like kinase inhibitor, a glycogen synthase kinase inhibitor, a L-type calcium channel agonist, and a DNA methylation inhibitor, as well as a leukemia inhibitory factor. Preferred combinations of additives include the combination of a mitogen-activated protein kinase kinase inhibitor and a glycogen synthase kinase inhibitor as well as a leukemia inhibitory factor, the combination of a mitogen-activated protein kinase kinase inhibitor, an activin receptor-like kinase inhibitor and a glycogen synthase kinase inhibitor as well as a leukemia inhibitory factor, the combination of a L-type calcium channel agonist and a DNA methylation inhibitor as well as a leukemia inhibitory factor, and the like.

The medium in the step (b) of the present invention can be prepared using a medium in common use for animal cell culture as the basal medium. Any basal medium for animal cell culture can be used; examples include BME medium, BGJb medium, CMRL 1066 medium, Glasgow MEM medium, Improved MEM Zinc Option medium, IMDM medium, Medium 199 medium, Eagle MEM medium, aMEM medium, DMEM medium, Ham F12 medium, RPMI 1640 medium, Fischer's medium, and mixtures thereof and the like.

The medium may be a serum-containing medium or a serum-free medium. A serum-free medium means a medium that does not contain unconditioned or unpurified serum; a medium containing a purified blood component or animal tissue component (e.g., growth factor), a medium supplemented with a serum replacement reagent (e.g., Knockout Serum Replacement (KSR; Invitrogen), etc) or the like is understood to be a serum-free medium.

The medium may also contain fatty acids or lipids, amino acids (e.g., nonessential amino acids), vitamins, growth factors, cytokines, antioxidants, 2-mercaptoethanol, pyruvic acid, buffering agents, minerals and the like.

Mitogen-activated protein (MAP) kinase kinase (MAPKK) catalyzes the phosphorylation of both the threonine residue and tyrosine residue, which are required for activation of MAP kinase; mammals have a MAP kinase known as ERK, and MAPKK is also called MEK (MAP kinase-ERK kinase) as it activates ERK. The choice of the MAPKK inhibitor is not particularly limited, as far as it possesses an action to inhibit MAPKK; examples include PD0325901, SB203580, SB22025, SB239063, SKF-86002 and the like, with preference given to PD0325901 and SB203580. The concentration of MAPKK inhibitor to the medium is, for example, 0.005 to 500 μM, preferably 0.05 to 50 μM.

Activin receptor-like kinase (ALK), an activator of receptors to which ligands belonging to the TGF-β superfamily bind, activates cytoplasm substrates to cause specific intracellular signal transduction. The activin receptor-like kinase occurs in the form of ALK1 to 7. Although the ALK inhibitor used in the present invention may be any inhibitor that inhibits any one thereof, ALK5 inhibitors are preferred. Examples of ALK5 inhibitors include A83-01, SB-431542, IN-1130, SM16, GW788388 and the like, with preference given to A83-01 and SB-431542. The concentration of ALK inhibitor added to the medium is, for example, 0.002 to 200 μM, preferably 0.02 to 20 μM.

A glycogen synthase kinase (GSK) phosphorylates an enzyme for promoting glycogen synthesis to regulate its activity. Of the glycogen synthase kinases, GSK3 is a multifunctional serine/threonine kinase occurring in all eukaryotic organisms, serving as an important regulator for many signal transduction pathways, including cellular responses to Wnt, tyrosine kinase and G protein conjugate receptors, and it is involved in a broad range of cell processes, from glycogen metabolism to cell cycle regulation and proliferation. In the present invention, GSK3 inhibitors are preferred GSK inhibitors, with greater preference given to GSK3β inhibitors. Examples of GSK3β inhibitors include CHIR99021, SB-415286, SB-2167, indirubin-3'-Monoxime, Kenpaullone and the like, with preference given to CHIR99021 and Kenpaullone. The concentration of GSK inhibitor to the medium is, for example, 0.03 to 300 μM, preferably 0.3 to 30 μM.

The L-type calcium channel is a potential-dependent calcium channel in heart muscle and vascular smooth muscles, genetically including 4 different isoforms of the $\alpha_1$ subunit. Examples of the L-type calcium channel agonist of the present invention include Bay K8644, Verapamil and the like, with preference given to Bay K8644. The concentration of L-type calcium channel agonist to the medium is, for example, 0.01 μM to 100 μM, preferably 0.1 μM to 10 μM.

DNA methylation is involved in the expressional control of epigenetic genes, in which DNA methyltransferase acts to add the methyl group to the 5-position carbon atom in the C (cytosine) base of DNA, resulting in the formation of methylated DNA. Examples of the DNA methylation inhibitor of the present invention include 5-azacytidine, 5-aza-2'-deoxycytidine, BIX-01294, RG108 and the like, with preference given to BIX-01294 and RG108. The concentration of DNA methylation inhibitor added to the medium is, for example, 0.1 nM to 1000 mM, preferably 1 nM to 10 mM.

Leukemia inhibitory factor (LIF), a cytokine in the interleukin 6 family, functions to inhibit the proliferation of leukemia cells, to increase platelets, to suppress the differentiation of embryonic stem cells, to proliferate undifferentiated hematopoietic precursor cells, and the like. Leukemia inhibitory factor is also known as leukocyte inhibitory factor or leukocyte migration inhibitory factor. The leukemia inhibitory factors used in the present invention are not limited as long as they can produce canine iPS cells in combination with one or more substance(s) selected from a mitogen-activated protein kinase kinase inhibitor, an activin receptor-like kinase inhibitor, a glycogen synthase kinase inhibitor, a L-type calcium channel agonist and a DNA methylation inhibitor, and may include leukemia inhibitory factors derived from any mammals such as canine, human, bovine, chimpanzee, rat and mouse. Preferably, a human or canine leukemia inhibitory factor can be used. The leukemia inhibitory factors can be obtained by any known method. Preferably, they can be obtained by performing RT-PCR using RNA prepared from a mammalian tissue as a template and a pair of primers designed based on the information on cDNA sequences of the leukemia inhibitory factors obtained from publically available databases. The mouse and human leukemia inhibitory factors can also be purchased from CHEMICON and the like. In the medium for the step (b) of the present invention, the leukemia inhibitory factor concentration can be set at, for example, 10 to 100000 U/mL, preferably 100 to 10000 U/mL.

The medium for the step (b) of the present invention may further contain a histone deacetylase (HDAC) inhibitor. The choice of HDAC inhibitor is not particularly limited, as far as it inhibits the enzyme for removing the acetyl group from acetylated histones; examples include valproic acid, butyric acid, trichostatin A, trapoxin A, HC-toxin, apicidin or salts thereof and the like, and one or more thereof can be used. Of these HDAC inhibitors, valproic acid or a salt thereof is preferred. The concentration of HDAC inhibitor added to the medium is, for example, 0.01 to 100 mM, preferably 0.1 to 10 mM.

The medium for use in the step (b) of the present invention may further contain basic fibroblast growth factor (bFGF), which is a cytokine in the family of fibroblast growth factors (FGFs) and functions to promote fibroblast proliferation, vascularization and other events in wounds. In the present invention, it is particularly preferable that the basic fibroblast growth factor be used, since it acts to contribute to the maintenance of the undifferentiated state of cells, and also since it enables production of more complete canine iPS cells when used simultaneously with the above-described leukemia inhibitory factor. The basic fibroblast growth factor is commercially available from Sigma Company and the like. The concentration of basic fibroblast growth factor added to the medium is, for example, 0.04 to 4000 ng/mL, preferably 0.4 to 400 ng/mL.

The medium for the step (b) may be further supplemented with an iPS cell induction improver other than those shown above, including, for example, p53 inhibitor, UTF1 [*Cell Stem Cell*, 3: 475-479 (2008)], Wnt signal inducer (e.g., soluble Wnt3a) [*Cell Stem Cell*, 3: 132-135 (2008)], vitamin C [*Cell Stem Cell. January* 8; 6(1): 71-9 (2010)], sodium butyrate and the like.

After being contacted with nuclear reprogramming factors, the canine somatic cell is subjected to the step (b) within, for example, 7 days (preferably within 6, 5, 4, or 3 days), particularly preferably within 48 hours.

Culture conditions for the step (b) of the present invention can be set as appropriate according to the medium used. For example, culturing temperature is not particularly limited, and is about 30 to 40° C., preferably about 37° C. $CO_2$ concentration is, for example, about 1 to 10%, preferably about 2 to 5%. The cultivation can be performed for about 3 weeks or more, preferably about 3 to 5 weeks, during which an ES cell-like colony is formed and amplified.

In the present invention, it is preferable that subculture on feeder cells be started after the ES cell-like colony has grown to a sufficient size following the elapse of 3 to 5 weeks after contact with the nuclear reprogramming factor. As feeder cells, fibroblasts treated with radiation or an antibiotic to terminate the cell division thereof [e.g., canine embryonic fibroblasts, mouse embryonic fibroblasts (MEFs)] and the like are useful. Examples of useful MEF include the STO cell, SNL cell [McMahon, A. P. & Bradley, A. *Cell* 62: 1073-1085 (1990)] and the like.

A candidate colony of canine iPS cells can be selected by a method with drug resistance and reporter activity as indicators, and also by a method based on visual examination of morphology. As an example of the former, a colony positive for drug resistance and/or reporter activity is selected using a recombinant canine somatic cell wherein a drug resistance gene and/or a reporter gene is targeted to the locus of a gene highly expressed specifically in pluripotent cells (e.g., Fbx15, Nanog, or Oct3/4).

When a nucleic acid is transferred as a nuclear reprogramming factor, the expression of a marker gene such as a drug resistance gene or a reporter gene, transferred at the same time as described above, may be used as an indicator.

The identity of the cells of a selected colony as iPS cells can be confirmed by, for example, alkaline phosphatase staining.

For example, cells of a colony formed in the step (b) are collected and immobilized on a plate or well, after which the cells may be brought into contact with a substrate, and the color developed is checked. Moreover, it is possible to perform tests such as analyzing the expression of various ES cell-specific genes by RT-PCR etc. and transplanting the cells selected to a mouse and confirming the formation of teratomas.

The present invention also enables the provision of canine pluripotent stem cells of somatic cell derivation possessing pluripotency and a potential for self-replication. Here, "pluripotency" means the capability of differentiating into all the three primary germ layers of the embryo, and "a potential for self-replication" means the capability of proliferation while maintaining the undifferentiated state. The canine pluripotent stem cells of somatic cell derivation are preferably canine iPS cells obtained by the above-described method of producing a canine iPS cell.

Although canine pluripotent stems cells of somatic cell derivation, preferably canine iPS cells, posses properties extremely similar to those of canine ES cells obtained via an embryo, they are thought to differ from canine ES cells in any one or more of properties, including, but are not limited to, epigenetic modification patterns of chromosome genes, such as DNA methylation status and histone acetylation, gene expression patterns, sensitivity to differentiation induction treatment, and tumorigenic potential at the time of transplantation. These property differences should be based on the derivation from a somatic cell, and on the process that involves reprogramming using a defined nuclear reprogramming factor (not including any unknown components of germ cells); therefore, the canine pluripotent stems cells of somatic cell derivation, preferably canine iPS cells, are distinguishable from canine ES cells induced from an early embryo or an embryo having a transplanted somatic cell nucleus, as they are defined as canine pluripotent stem cells "of somatic cell derivation" or canine "iPS cells".

Considering the fact that the canine iPS cell of the present invention is more preferably used not only for medical purposes in dogs, but also for animal experimentation for confirming the safety and efficacy of human iPS cells before their clinical application, canine iPS cells obtained by transferring reprogramming genes (e.g., 4 factors consisting of Oct3/4 gene, Sox2 gene, Klf4 gene and c-Myc gene, 3 factors consisting of Oct3/4 gene, Sox2 gene and Klf4 gene), using a retrovirus or lentivirus, which currently reportedly offers the most efficient establishment of human iPS cells, are useful for this purpose. Because transfection using a retrovirus or lentivirus involves the integration of reprogramming genes in the genome, the canine iPS cells thus obtained are clearly distinct, in terms of genome structure, not only from the starting canine somatic cell, but also from canine ES cells. Of course, even when a reprogramming gene has been transferred using an adenovirus or plasmid, the canine iPS cell of the present invention incorporating the reprogramming gene may be generated using whatever vector is used for transfection, because even these vectors, which are essentially only rarely integrated in the genome because of the high selection pressure at the time of iPS colony induction, tend to produce iPS cells having the reprogramming gene integrated in the genome thereof. Furthermore, when using an episomal vector capable of self-replication outside the chromosome, the reprogramming gene can be genetically stably present in iPS cells, although it is not integrated onto the genome, the canine iPS cells obtained using such vectors are also encompassed in the scope of the present invention.

Preferably, reprogramming genes that are genetically stably present in the canine iPS cell of the present invention are at least one gene selected from among the Oct3/4 gene, Sox2 gene, Klf4 gene and c-Myc gene. Preference is given to 4 factors consisting of Oct3/4 gene, Sox2 gene, Klf4 gene and c-Myc gene, or 3 factors consisting of Oct3/4 gene, Sox2 gene and Klf4 gene. Here, "a reprogramming gene" means an exogenous gene that acts for the sake of nuclear reprogramming in a somatic cell; substantially the same genes therewith that are "intrinsically present" in canine somatic cells are of course not included in the scope of reprogramming genes.

The canine iPS cell thus established can be used for varied purposes. For example, by utilizing a method of differentiation induction reported with respect to ES cells, differentiation into various cells (e.g., myocardial cells, blood cells, nerve cells, vascular endothelial cells, insulin-secreting cells and the like) from canine iPS cells can be induced. Therefore, inducing canine iPS cells using a somatic cell collected from a patient animal or another animal of the same MHC type would enable stem cell therapy by autogeneic or allogeneic transplantation, wherein the iPS cells are differentiated into desired cells (that is, cells of an affected organ of the patient animal, cells that have a therapeutic effect on disease, and the like), which are transplanted to the patient animal. The transplantation therapy described above is particularly useful not only for practical purposes in veterinary medicine, but also in animal experimentation for testing the efficacy and safety of similar cell transplantation therapy for humans using human iPS cells.

Furthermore, since functional cells (e.g., hepatocyte) differentiated from a canine iPS cell are believed to reflect the status of the functional cells in the actual body more than do the corresponding existing cell line, they can also be suitably used in in vitro evaluation screening etc. for the pharmacological efficacy and toxicity of drug candidate compounds. Additionally, there is no need of resecting organs or tissues from laboratory dogs to prepare primary functional cells, an aspect desirable from the viewpoint of animal welfare.

EXAMPLES

The present invention is hereinafter described more specifically by means of the following Examples, which, however, are for illustrative purposes only and do not limit the scope of the invention in any way.

Example 1

Construction of Retroviral Vectors

Primers were designed on the basis of cDNA sequence information registered with a public database, and each of the canine genes Oct3/4, Klf4, Sox2, and c-Myc was amplified by RT-PCR from RNA extracted from cerebrum, retina, gastric mucosa, skin, skeletal muscle, lung, and testis. Since Sox2 was not amplified well, a comparison was made between the predicted canine Sox2 sequence and human Sox2 sequence on the database; it was found that an extra sequence of 165 amino acids was present at the N-terminus of canine Sox2. Then, this extra portion was removed to re-design a primer, using which RT-PCR was performed with successful results of amplification of the canine Sox2 gene. The sequences of the primers used for the PCR amplification are shown in Table 1.

TABLE 1

| Primer Set | Primer | Primer length (bp) | Base sequence (5' → 3') | Reference sequence |
|---|---|---|---|---|
| C-KLF4 | KLF4-F | 40 | TTAATTAAGGATCCACCATGGCTGTCAGCGACGCTCTGCT | SEQ ID NO: 9 |
|  | KLF4-R | 42 | GGCCTGCAGGAATTCTTAAAAGTGC-CTCTTCATGTGTAAGGC | SEQ ID NO: 10 |
| C-OCT4 | OCT4-F | 40 | TTAATTAAGGATCCACCATGGCGGGACACCTGCTCTTCCGA | SEQ ID NO: 11 |
|  | OCT4-R | 40 | GGCCTGCAGGAATTCTCAATTTGAATGCATGGGAGAGCCC | SEQ ID NO: 12 |
| C-SOX2 | F136 | 24 | ATGTACAACATGATGGAGACGGGAG | SEQ ID NO: 13 |
|  | R2 | 24 | TCACATGTGCGAGAGGGGCAGTGT | SEQ ID NO: 14 |
| C-C-Myc | C-Myc-F | 40 | TTAATTAAGGATCCACCCTGGATCTCCTCCGGAGAGTGGA | SEQ ID NO: 15 |
|  | C-Myc-R | 40 | GGCCTGCAGGAATTCTTAGGCACCAGAGTTCCTTAGCTGT | SEQ ID NO: 16 |

The base sequences of the respective genes obtained were determined by a conventional method. The results are shown in the sequence listing (SEQ ID NO:1 to 8). As expected, canine Sox2 was found to encode an amino acid sequence resulting from deletion of the 165 N-terminal amino acids from the predicted sequence on the database. Canine Klf4 was found to have an inserted sequence of about 90 amino acids that is not present in the predicted sequence of canine Klf4 on the database. Because human and mouse Klf4 have sequences corresponding to the 90-amino-acid sequence, showing that the predicted sequence of canine Klf4 on the database was likely to be an error.

Each of the amplified genes was inserted into the multicloning site of pMXs-IRES-GFP (FIG. 1c) to obtain four retroviral vectors harboring the respective genes.

Example 2

Preparation of Virus

100 μL of the Fugene 6 transfection reagent (Roche) was placed in a 10 cm Petri dish containing $6 \times 10^4$ previously seeded Plat-GP cells, and the dish was allowed to stand at room temperature for 5 minutes. Subsequently, each retroviral vector and 3 μg of pCMV-VSVG were added, and the dish was further allowed to stand at room temperature for 15 minutes, after which the dish was added to a culture broth for Plat-GP cells. The cells were cultured at 37° C. in the presence of 5% $CO_2$ using the culture broth of a DME medium (Invitrogen) supplemented with 0.5% antibiotic and 10%

FBS (final concentrations). The medium was replaced with a fresh supply 24 hours after transfection. The culture supernatant was recovered 48, 60, and 72 hours after transfection, and the recovered supernatants were combined to obtain a virus-containing liquid. The virus-containing liquid was filtered through a 0.45 µm Millipore filter, and polybrene was added at 4 µg/mL to yield a viral liquid.

Example 3

Efficiency of Transfection Using Retroviral Vector

Canine fibroblasts were obtained by extirpating a fetus from a beagle dog at day 30 of gestation (purchased from ORIENTAL BIO Co., Ltd.), and shredding and enzymatically treating the fetal tissue. The canine fibroblasts were transfected with a reprogramming gene by retroviral infection, and the GFP expression level after the infection was analyzed by flow cytometry. On day 5 after the infection, about 60% of the fibroblasts became positive for GFP, demonstrating highly efficient transfer of the gene (FIGS. 2 and 3).

Example 4

Generating Canine iPS Cells

Four genes consisting of Oct3/4, Sox2, Klf4, and c-Myc were transferred to a canine fibroblast using retroviral vectors. Upon completion of the 3rd infection, the culture supernatant was replaced with a fresh supply [culture medium for primate ES cell+LIF (1000 U/ml)+bFGF (6 ng/ml)+PD0325901 (0.5 µM)+A-83-01 (0.25 µM)+CHIR99021 (3 µM)+valproic acid (1 mM)]. On day 2 after the transfection, about 60% of the fibroblasts became positive for GFP. On day 5 after the transfection, small GFP-positive colonies were also observed (FIG. 4c). On day 20 after the transfection, formation of colonies assuming a monolayer structure was observed. The colonies identified were morphologically similar to those of canine ES cells. About 1 month after the transfection, the colonies reached a size allowing mechanical detachment. Thereafter, the cells were subcultured on feeder cells derived from mouse embryonic fibroblasts. The mouse embryonic fibroblasts had been obtained by shredding and enzymatically treating fetal tissue from a pregnant mouse at day 13 of gestation. The mouse embryonic fibroblasts for use as feeder cells had been treated with mitomycin C, and 1.5× $10^6$ cells were seeded to a 10 cm dish on the day before starting the subculture of the canine iPS cells.

Example 5

Expression of ES Cell Markers in Canine iPS Cells

Immunostaining analysis was performed to confirm the expression of ES cell markers. Canine iPS cells were fixed by a reaction with 4% paraformaldehyde for 30 minutes. The cells fixed were washed with PBS, and pre-treated with 2% FBS and 0.2% Triton X-100/PBS. Anti-Oct3/4 antibody (SANTA CRUZ, diluted 100 folds), anti-SSEA-1 antibody (Millipore, diluted 50 folds), anti-SSEA-4 antibody (Millipore, diluted 50 folds), anti-TRA-1-60 antibody (Millipore, diluted 50 folds), and anti-TRA-1-81 antibody (Millipore, diluted 50 folds) were used as primary antibodies. TRITC-labeled anti-mouse antibody was used as a secondary antibody. Nuclei were stained with 1 µg/ml DAPI (Roche).

Figures 1, 10:
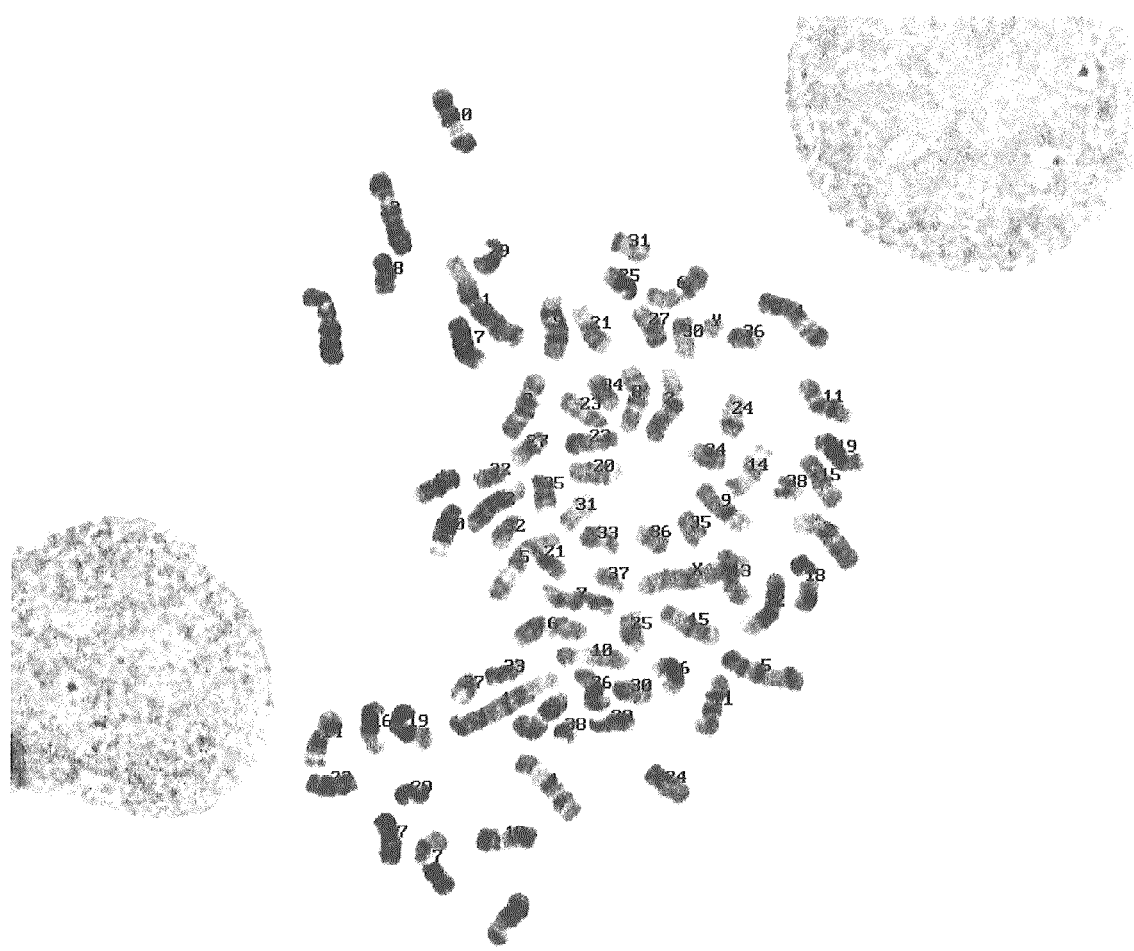
Figures 2, 10:
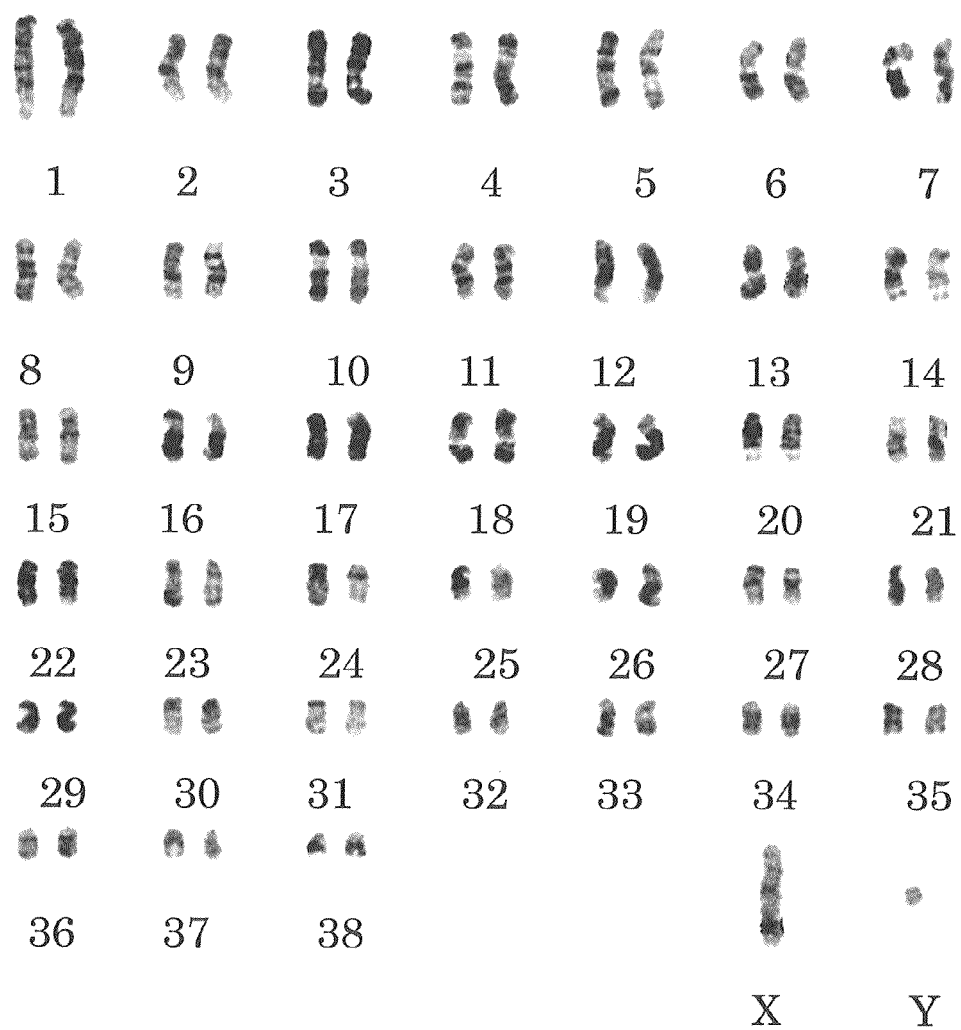
FIG. 10 shows results of karyotype analysis of a canine iPS cell.

In the immunostaining, the tested canine iPS cells showed positive for Oct3/4, SSEA-4, TRA-1-60 and TRA-1-81, exhibiting the same expression pattern as with canine ES cells (FIGS. 6-1 and 6-2).

Example 6

Alkaline Phosphatase Staining

Alkaline phosphatase staining was performed using the Leukocyte Alkaline Phosphatase Kit (Sigma). For control, the mouse iPS cell line iPS-MEF-Ng-20D-17 (supplied by Professor Shinya Yamanaka at Kyoto University) was used. In the staining, the tested canine iPS cells showed positive for alkaline phosphatase, and the intensity of the staining exhibited to be similar to that of mouse iPS cells (FIG. 7).

Example 7

Induction of Differentiation from iPS Cells to Ectodermal, Mesodermal and Endodermal Cells To confirm that canine iPS cells are capable of differentiating into all the three primary germ layers of the embryo, the following experiments were performed. To induce differentiation into the ectoderm, canine iPS cells were cultured for 14 days using the GME (Glasgow Minimum Essential) medium supplemented with 10% KSR, 0.1 mM non-essential amino acids, 1 mM pyruvate, 0.2 mM 2-mercaptoethanol, 100 nM Vitamin B12, 33 µg/ml heparin, and 0.5% penicillin/streptomycin (final concentrations). To induce differentiation into the mesoderm, the cells were cultured for 10 days on a type IV collagen-coated dish containing the α-ME (α-minimum essential) medium supplemented with 10% fetal calf serum, $5 \times 10^{-5}$ mol/l 2-mercaptoethanol, 0.5% penicillin/streptomycin, and 100 ng/ml VEGF (final concentrations). To induce differentiation into the endoderm, the cells were cultured for 14 days using the DME (Dulbecco's modified Eagle's) medium supplemented with 20% KSR, 1 mM non-essential amino acids, 0.55 mM 2-mercaptoethanol, 0.5% penicillin/streptomycin, 4 ng bFGF, 1% glutamine, and 100 ng activin A (final concentrations).

The differentiation-induced cells were fixed with a PBS containing 4% paraformaldehyde, and incubated in a PBS containing 5% normal goat antibody or donkey serum (Chemicon), 1% bovine serum albumin (Nacalai Tesque), and 0.2% Triton X-100. Anti-α-fetoprotein antibody (1:500, Dakocytomation), anti-FLK1 antibody (1:500, Upstate), and anti-βIII-tubulin:antibody (1:500, Sigma) were used as primary antibodies. TRITC-labeled anti-rabbit antibody was used as a secondary antibody. Nuclei were stained with 1 µg/ml DAPI (Roche). The results of the immunostaining showed that the canine iPS cell generated is capable of differentiating into the three primary germ layers of the embryo, i.e., ectoderm, mesoderm and endoderm, and has hence pluripotency (FIG. 8).

Example 8

Microarray Analysis

Figure 9:
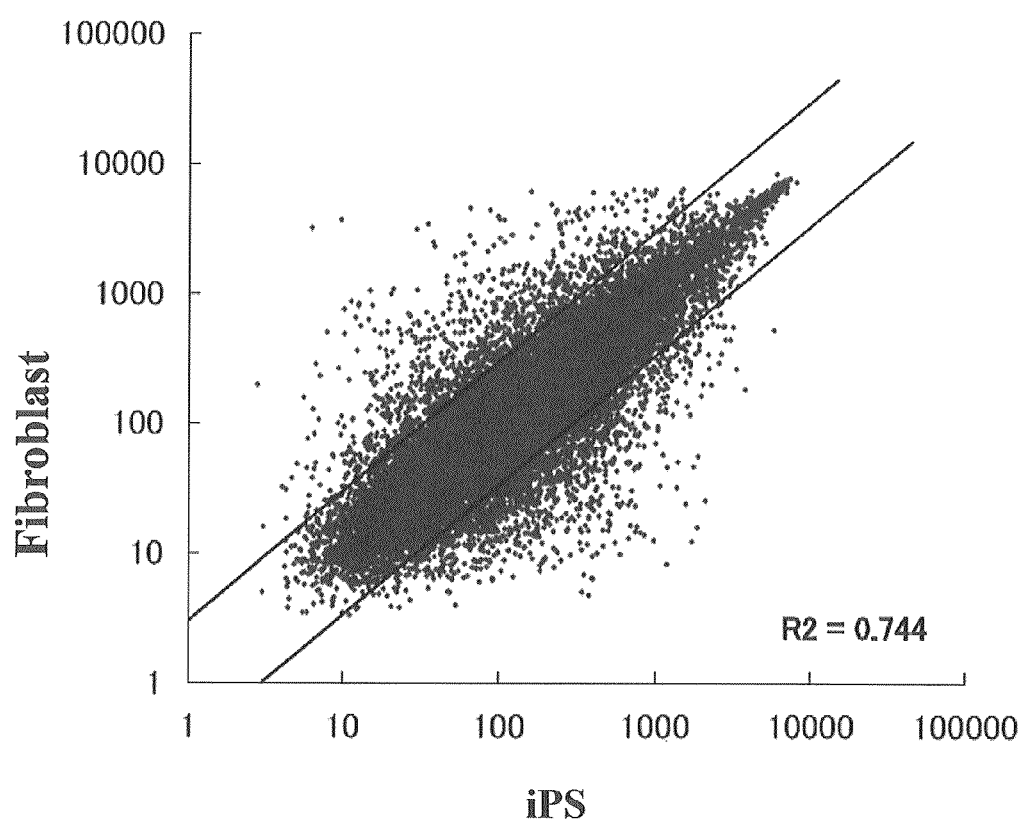
FIG. 9 is a graphic representation of microarray analysis of the gene expression patterns of a canine iPS cell and the fibroblast before becoming the canine iPS cell.

To determine whether the gene expression pattern differs between a canine iPS cell and the starting canine fibroblast from which the canine iPS cell has been generated, DNA microarray analysis was performed using total RNAs from the canine iPS cell and canine fibroblast, as described in *Cell*, 131, 861-872 (2007). The results are shown in FIG. 9. An attempt to detect genes expressed specifically in the canine iPS cell revealed overexpression of the ES cell-specific genes Sox2 (×600) and Sall4 (×1600). These results confirmed that the gene expression pattern differed between the canine iPS cell and the starting canine fibroblast (FIG. 9).

Example 9

Karyotype Analysis

A colcemide solution was added to canine iPS cells, and the canine iPS cells were cultured for several hours. After the cells were monodispersed by trypsinization, the cells and nuclei were swollen with potassium chloride solution, and fixed with Carnoy's solution. After Q band treatment, the chromosomes were microphotographed, and karyograms were generated.

In the present invention, the number of chromosomes in the canine iPS cell was determined to be 78, confirming that the canine iPS cell established herein was derived from a canine somatic cell. No chromosomal aberrations were observed (FIG. 10).

Example 10

A procedure for Efficiently Selectively Generating Canine iPS Cell Colonies

By adding a plurality of low molecular compounds along with nuclear reprogramming factors, generation of iPS cell colonies was induced efficiently. Four genes consisting of Oct3/4, Sox2, Klf4, and c-Myc were transferred to a canine fibroblast using retroviral vectors. After completion of the 3rd transfection, the culture broth was replaced [culture medium for primate ES cell+LIF (1000 U/ml)+bFGF (6 ng/ml)+valproic acid (0.5 mM)+Bay K8644 (1 µM)+BIX01294 (0.5 µM)+RG108 (0.02 µM)].

Figure 11:
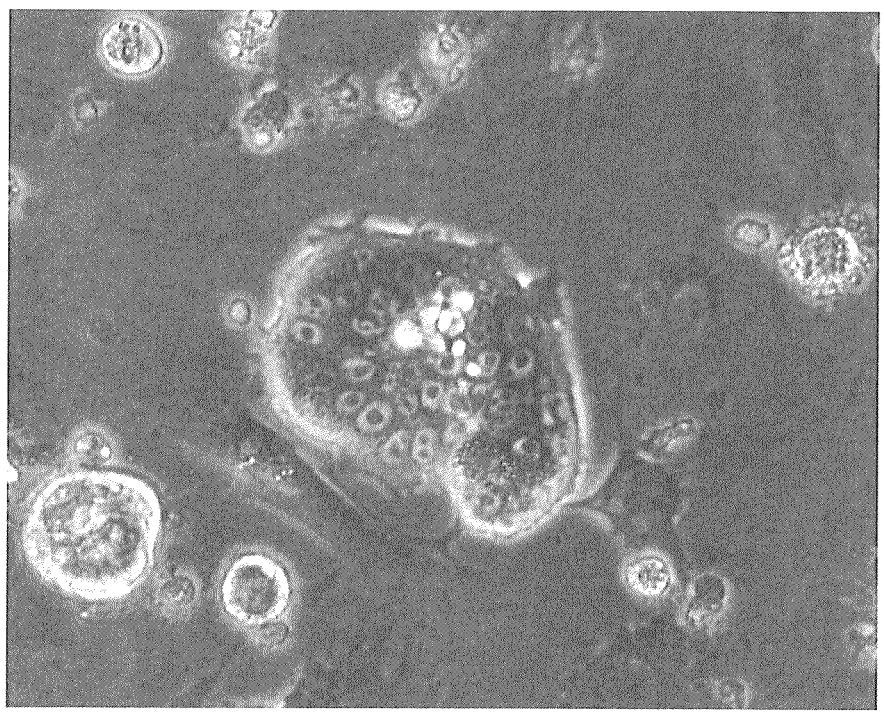
FIG. 11 is a photomicrograph of colonies that emerged on day 4 after the start of cultivation with Bay K8644, BIX01294, RG108, and valproic acid added to the medium on day 2 after transfer of Oct3/4, Sox2, Klf4, and c-Myc.

Nearly all colonies visible on day 4 after transfection were colonies like those of canine ES cells. This result confirmed that by transferring the plurality of low molecular compounds, along with the reprogramming factors, to the cell, canine iPS cells were obtained efficiently (FIG. 11).

Example 11

Preparation of Canine LIF

A recombinant canine LIF was prepared using a vaculovirus basically according to Nagata [*Methods in Molecular Biology*, 577: 109-20 (2009)]. Briefly, total RNA was extracted from tissues (skin, muscle and testis) excised from an adult beagle under anesthesia with ketamine hydrochloride and xylazine. RT-PCR was performed using this RNA as a template and primers designed based on the information on canine LIF cDNA sequence registered in the NCBI database (XM_534732), and a canine LIF cDNA with 6×His tag at the N-terminus was amplified by Nested PCR. The primers used in PCR amplification are shown in Table 2. The first PCR was performed using F01-primer and R-primer, and the second PCR was performed using F02-primer and R-primer.

TABLE 2

| Primer | Primer length(bp) | Base sequence (5' → 3') | Reference sequence |
|---|---|---|---|
| F01-primer | 21 | GGCTCCAGTATATAAATCAGG | SEQ ID NO: 17 |
| F02-primer | 21 | AAACTGCCGGCATCTAAGGTC | SEQ ID NO: 18 |
| R-primer | 29 | CTAGAAGGCCTGGGCCACCACGGCAATGA | SEQ ID NO: 19 |

Figure 12:
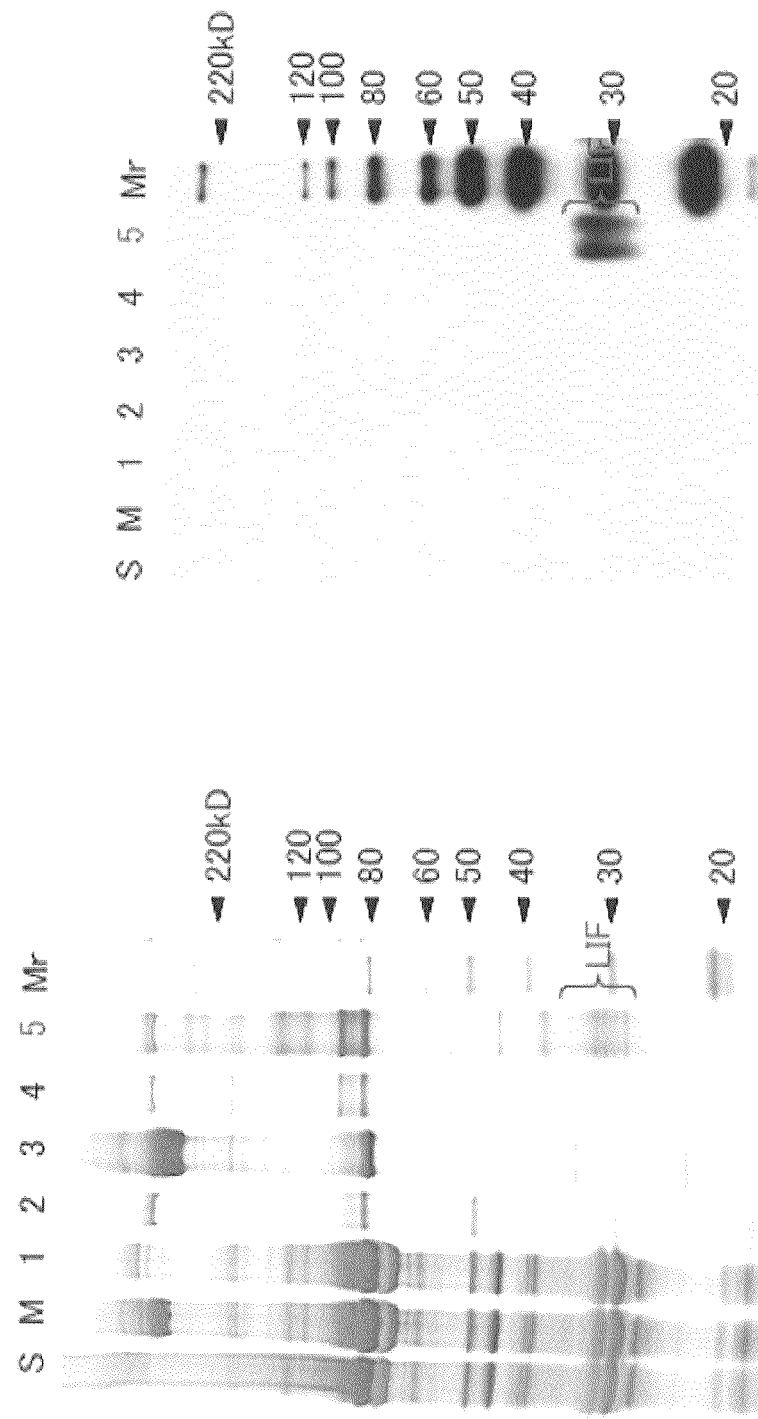
FIG. 12 shows preparation of a recombinant canine LIF protein using a silkworm-vaculovirus expression system. Proteins from a body fluid of silkworms infected with a recombinant vaculovirus expressing canine LIF were electrophoresed in gel, and subjected to silver staining (left panel) and Western blot analysis (right panel). A part of the body fluid collected from LIF-expressing silkworms was loaded on lane S, and the rest was diluted three-fold with a dilution buffer (50 mM Tris-HCl, 300 mM NaCl, 20 mM imidazole, pH 8.0) and deionized. A part of the diluted solution was loaded on lane M, and the rest was subjected to an iMAC with Ni-carrier and the passed fraction (lane 1) was collected. The Ni-carrier was washed with a washing buffer (50 mM Tris-HCl, 300 mM NaCl, 20 mM imidazole, pH 8.0) and the passed fraction (lane 2) was collected. Then, the proteins adsorbed to the Ni-carrier were eluted with a stepwise gradient of imidazole (50, 80 and 250 mM in 50 mM Tris-HCl, 300 mM NaCl, pH 8.0) to give three eluted fractions (lane 3: 50 mM imidazole eluate, lane 4: 80 mM imidazole eluate, lane 5: 250 mM imidazole eluate).

The amplified canine LIF cDNA fragment was cloned into a cloning vector and the resulting vector was co-transfected into BmN cells derived from *Bombyx mori* with a vaculovirus-derived DNA. The recombinant vaculoviruses expressing canine LIF were obtained from the culture supernatant of BmN cells 6 days after transfection. Silkworms were infected with the recombinant vaculoviruses and body fluids were extracted from the silkworms 6 days after infection to give canine LIF protein. The canine LIF protein obtained was electrophoresed in SDS-polyacrylamide gel and confirmed by silver staining and Western blotting using an anti-His tag antibody (FIG. 12, lane 5).

Example 12

Production of Canine iPS Cells from Adipose-Derived Cells

Canine adipose-derived cells used in the production of iPS cells were obtained by the following method.

A part of omental tissue was excised from an adult beagle under anesthesia with ketamine hydrochloride and xylazine and the resulting omental tissue was treated with a digestion solution (10 mL of Hank's buffer solution containing 30 mg of type 8 collagenase (Sigma), 1.3 mg/mL glucose, 0.4 g of bovine albumin fraction 5 (Sigma) and adipose tissue alone was collected. The adipose tissue was neutralized with D-MEM containing fetal bovine serum, treated with an erythrolysis solution and centrifuged to give cell aggregates. These cell aggregates were used as adipose-derived cells hereinafter.

The production of canine iPS cells from the adipose-derived cells was performed by the following method.

Four kinds of retroviruses carrying mouse-derived Oct3/4, Sox2, Klf4 and c-Myc gene, respectively, (supplied by Addgene, Inc.), were introduced into the adipose-derived cells. Upon completion of the 3rd infection, the culture supernatant was replaced with a fresh supply [culture medium for primate ES cell (Reprocell)+canine LIF (20 ng/mL)+CHIR99021 (3 µM)+PD0325901 (0.5 µM)]. On day 14 after the initiation of infection, the emergence of canine ES cell-like colonies was confirmed (FIG. 13). Thereafter, the colonies were transferred onto a dish in which mouse embryo-derived fibroblasts had been pre-seeded and continuously cultured.

Since the number of colonies emerged remarkably increased in comparison with canine iPS cells derived from fibroblasts, it is suggested that use of adipose-derived cells as somatic cells and canine LIF increases the establishment efficiency of canine IFS cells.

Example 13

Expression of Markers for ES Cell in Canine iPS Cells Established from Adipose-Derived Cells RNA was extracted from the canine iPS cells obtained in Example 12 using quick gene 800 (Fuji film) and cDNA was synthesized with High Capacity RNA-to cDNA Master Mix (ABI). The expression of ES cell-specific genes in the canine iPS cells was analyzed by a quantitative real-time PCR using the resulting cDNA as a template. Out of the primers used in PCR, the primers for canine Oct3/4, canine Sox2, canine Eras and canine Tert were purchased from Applied Biosystems, Inc., the other primers (for canine Nanog and canine Rex1) were designed based on the information on canine Nanog and Rex1 sequence registered in the publically available databases (XM_543828 (NCBI database) for canine Nanog; ENSCAFG00000025203 (Ensembl database) for canine Rex1). The primers for canine Nanog and Rex1 are shown in Table 3.

TABLE 3

| Primer Set | Primer | Primer length(bp) | Base sequence (5' → 3') | Reference sequence |
|---|---|---|---|---|
| canine Nanog | F-primer | 24 | CCCAGCTUATGTTCTCAATGATC | SEQ ID NO: 20 |
| | R-primer | 22 | TCTTGCATCTGCTGGAGACTGA | SEQ ID NO: 21 |
| canine Rex1 | F-primer | 20 | TCGTCCATGGTCCTCGAGAT | SEQ ID NO: 22 |
| | R-primer | 20 | AGTTTCGCACGCTCATTGAA | SEQ ID NO: 23 |

Figure 14:
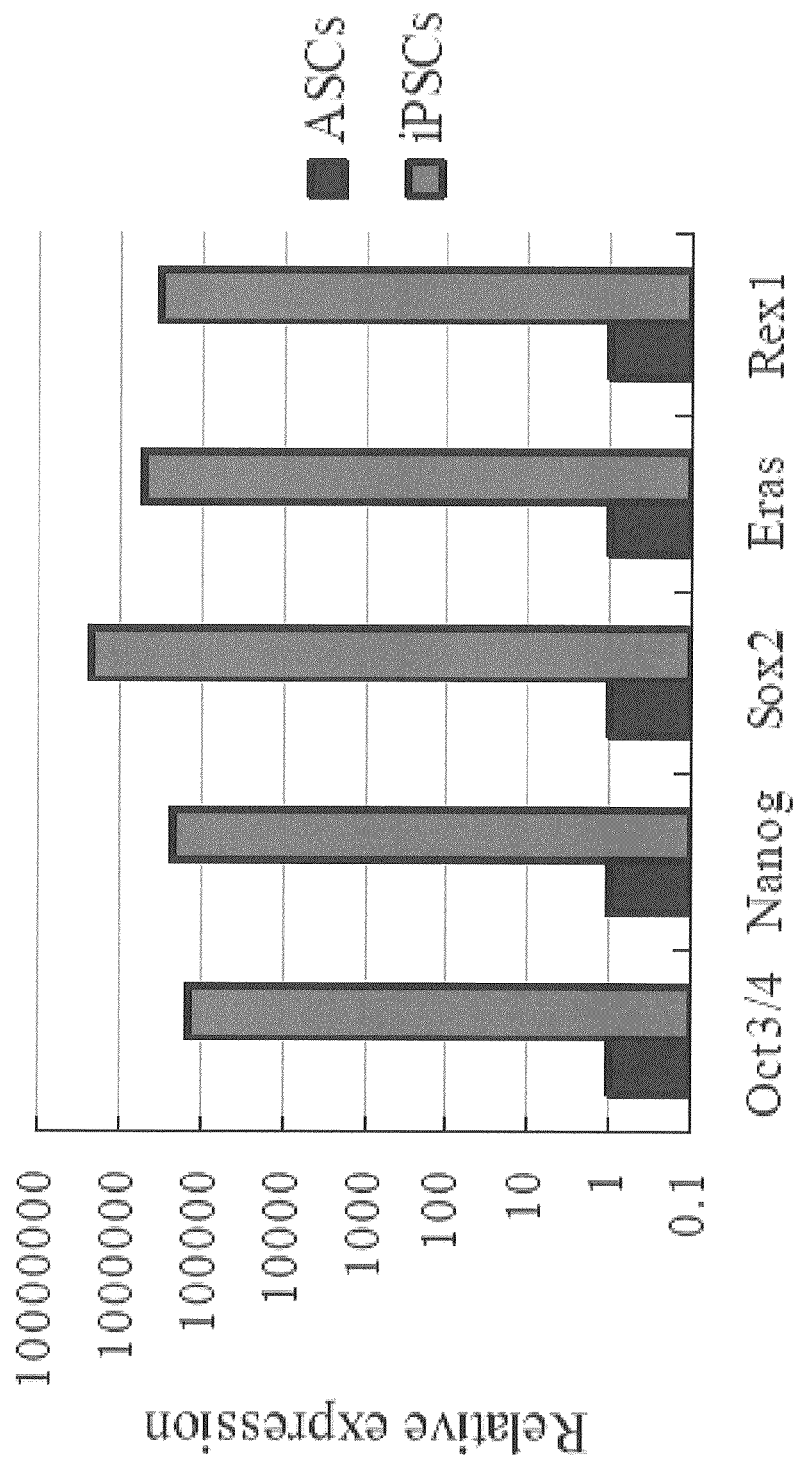
FIG. 14 shows the expression of ES cell-specific genes in canine iPS cells established from adipose-derived cells. The expression of Oct3/4, Nanog, Sox2, Eras and Rex1 in the iPS cells (iPSCs) and the original adipose-derived (stromal) cells (ASCs) was determined by a quantitative real-time PCR. The results are shown as relative expression levels when each of the expression levels of the marker genes in ASCs is defined as 1.

As a result of the quantitative real-time PCR, established canine iPS cells showed an elevated expression of Oct3/4, Nanog, Sox2, Eras and Rex1 compared to the original adipose-derived cells (FIG. 14).

Example 14

Figure 15:
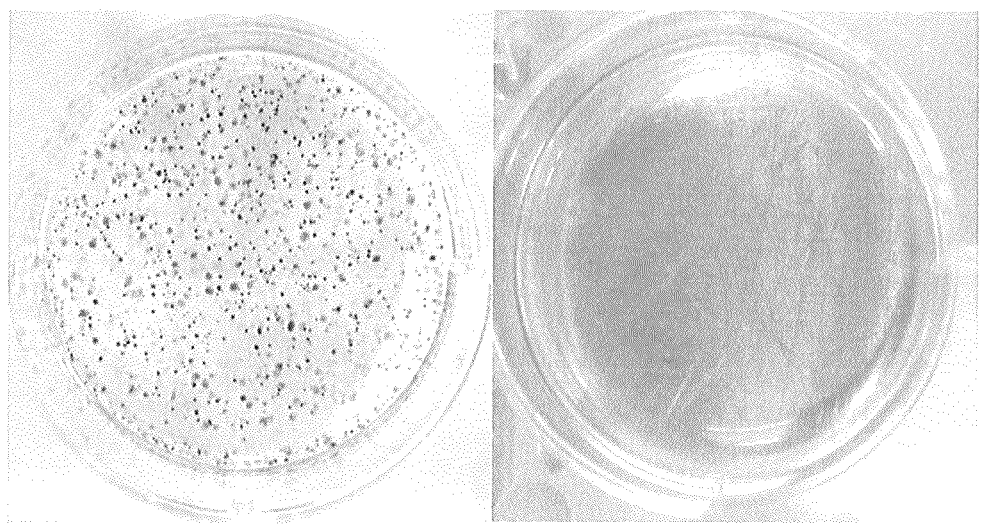
FIG. 15 shows the results of alkaline phosphatase staining of canine iPS cells established from adipose-derived cells. Left: canine iPS cells; Right: original adipose-derived cells as a negative control.

Alkaline Phosphatase Staining of Canine iPS Cells Established from Adipose-Derived Cells Alkaline phosphatase staining of the canine IFS cells obtained in Example 12 was performed in the same manner as in Example 6. As a result, the canine IFS cells obtained showed an increased alkaline phosphatase-positive cell ratio in comparison with a negative control (FIG. 15).

While the present invention has been described with emphasis on preferred embodiments, it is obvious to those skilled in the art that the preferred embodiments can be modified. The present invention intends that the present invention can be embodied by methods other than those described in detail in the present specification. Accordingly, the present invention encompasses all modifications encompassed in the gist and scope of the appended "CLAIMS."

In addition, the contents disclosed in any publication cited herein, including patents and patent applications, are hereby incorporated in their entireties by reference, to the extent that they have been disclosed herein.

What is claimed is:

1. A method of altering the differentiation state of a canine somatic cell to a less differentiated state, comprising:
   (a) transfecting the canine somatic cell with a retroviral vector comprising nucleic acids encoding each of Oct3/4, Sox2, Klf4, and c-Myc operably linked to a promoter, and
   (b) culturing the cell in a medium containing a mitogen-activated protein kinase kinase inhibitor, an activin receptor-like kinase inhibitor, a glycogen synthase kinase inhibitor, a histone deacetylase inhibitor, a basic fibroblast growth factor, and a leukemia inhibitory factor to provide a resultant canine cell,
   wherein the resultant canine cell (i) has an altered fate potential relative to the starting canine somatic cell, (ii) has a morphology similar to a canine ES cell, (iii) expresses Oct3/4, Sox2, Sall4, SSEA-4, TRA-1-60, and TRA-1-81 genes, (iv) is positive for alkaline phosphatase activity, (v) maintains normal karyotype, and (vi) has a potential to differentiate into a βIII-tubulin-expressing ectodermal cell, a FLK1-expressing mesodermal cell, and an α-fetoprotein-expressing endodermal cell.

2. The method according to claim 1, wherein the somatic cell is a fibroblast.

3. The method according to claim 1, wherein the activin receptor-like kinase inhibitor is an activin receptor-like kinase 5 inhibitor.

4. The method according to claim 1, wherein the glycogen synthase kinase inhibitor is a glycogen synthase kinase 3β inhibitor.

5. The method according to claim 1, wherein the histone deacetylase inhibitor is valproic acid or a salt thereof.

6. The method according to claim 1, wherein the culturing in step (b) is performed within 48 hours after transfection of the canine somatic cell with the retroviral vector in step (a).

7. The method according to claim 1, further comprising subculturing the resultant canine cell on feeder cells after the elapse of 3 to 5 weeks after transfection of the canine somatic cell with the retroviral vector in the step (a).

* * * * *